(12) United States Patent
Knick et al.

(10) Patent No.: US 11,230,576 B2
(45) Date of Patent: Jan. 25, 2022

(54) ALKALINE STABLE IMMUNOGLOBULIN-BINDING PROTEINS

(71) Applicant: Navigo Proteins GmbH, Halle/Saale (DE)

(72) Inventors: Paul Knick, Halle/Saale (DE); Erik Fiedler, Halle/Saale (DE); Ulrich Haupts, Halle/Saale (DE); Maren Meysing, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 299 days.

(21) Appl. No.: 16/324,651

(22) PCT Filed: Aug. 7, 2017

(86) PCT No.: PCT/EP2017/069976
§ 371 (c)(1),
(2) Date: Feb. 11, 2019

(87) PCT Pub. No.: WO2018/029157
PCT Pub. Date: Feb. 15, 2018

(65) Prior Publication Data
US 2019/0177376 A1  Jun. 13, 2019

(30) Foreign Application Priority Data

Aug. 11, 2016 (EP) ..................................... 16183710
Dec. 21, 2016 (EP) ..................................... 16205707

(51) Int. Cl.
| | | |
|---|---|---|
| C07K 1/22 | (2006.01) | |
| C07K 16/06 | (2006.01) | |
| C07K 14/31 | (2006.01) | |
| C07K 17/00 | (2006.01) | |

(52) U.S. Cl.
CPC ................ *C07K 14/31* (2013.01); *C07K 1/22* (2013.01); *C07K 16/065* (2013.01); *C07K 17/00* (2013.01)

(58) Field of Classification Search
CPC ...... C07K 14/31; C07K 16/065; C07K 17/00; C07K 1/22
See application file for complete search history.

(56) References Cited

U.S. PATENT DOCUMENTS

| | | | |
|---|---|---|---|
| 4,873,192 A | 10/1989 | Kunkel | |
| 5,789,166 A | 8/1998 | Bauer et al. | |
| 5,958,684 A | 9/1999 | Van Leeuwen et al. | |
| 6,217,863 B1 | 4/2001 | Godavarti et al. | |
| 6,569,677 B1 | 5/2003 | Legrand et al. | |
| 6,620,587 B1 | 9/2003 | Taussig et al. | |
| 6,673,901 B2 | 1/2004 | Koide | |
| 6,799,121 B2 | 9/2004 | Chu et al. | |
| 7,250,297 B1 | 7/2007 | Beste et al. | |
| 7,273,924 B1 | 9/2007 | Neri et al. | |
| 7,393,918 B2 | 7/2008 | Golemi-Kotra et al. | |
| 7,601,803 B1 | 10/2009 | Fiedler et al. | |
| 7,838,629 B2 | 11/2010 | Fiedler et al. | |
| 7,851,599 B2 | 12/2010 | Menrad et al. | |
| 8,097,254 B2 | 1/2012 | Neri et al. | |
| 8,404,814 B2 | 3/2013 | Neri et al. | |
| 8,426,357 B2 | 4/2013 | Kraehmer et al. | |
| 8,455,625 B2 | 6/2013 | Neri et al. | |
| 8,592,144 B2 | 11/2013 | Fiedler et al. | |
| 8,592,179 B2 | 11/2013 | Schraeml et al. | |
| 8,623,373 B2 | 1/2014 | Zardi et al. | |
| 8,748,351 B2 | 6/2014 | Kunert et al. | |
| 8,790,895 B2 | 7/2014 | Fiedler et al. | |
| 8,791,238 B2 | 7/2014 | Fiedler et al. | |
| 8,921,304 B2 | 12/2014 | Steuernagel et al. | |
| 9,492,572 B2 | 11/2016 | Nerkamp et al. | |
| 9,920,098 B2 | 3/2018 | Yoshida et al. | |
| 10,858,405 B2 | 12/2020 | Bosse-Doenecke et al. | |
| 2003/0045681 A1 | 3/2003 | Neri et al. | |
| 2003/0073623 A1 | 4/2003 | Drmanac et al. | |
| 2004/0043386 A1 | 3/2004 | Pray et al. | |
| 2006/0058510 A1 | 3/2006 | Skerra et al. | |
| 2006/0099686 A1 | 5/2006 | Fiedler et al. | |
| 2007/0015248 A1 | 1/2007 | Anton et al. | |
| 2007/0111287 A1 | 5/2007 | Fiedler et al. | |

(Continued)

FOREIGN PATENT DOCUMENTS

| | | |
|---|---|---|
| AU | 2013318928 | 4/2015 |
| EP | 1 591 527 A1 | 11/2005 |

(Continued)

OTHER PUBLICATIONS

Notice of Allowance corresponding to U.S. Appl. No. 15/548,976 dated Jul. 23, 2020.
Notice of Allowance corresponding to U.S. Appl. No. 15/744,054 dated Jan. 9, 2020.
Notice of Allowance corresponding to U.S. Appl. No. 15/744,147 dated Aug. 17, 2020.
Office Action corresponding to U.S. Appl. No. 15/744,147 dated Apr. 1, 2020.

(Continued)

*Primary Examiner* — James H Alstrum-Acevedo
*Assistant Examiner* — Erinne R Dabkowski
(74) *Attorney, Agent, or Firm* — Jenkins, Wilson, Taylor & Hunt, P.A.

(57) ABSTRACT

The present invention relates to immunoglobulin (Ig) binding proteins comprising one or more Ig binding domains with amino acids selected from the group consisting at least of 1I, 11A, 11E, 11I, 35R, 35I, and 42L. The invention further relates to affinity matrices comprising the Ig binding proteins of the invention. The invention also relates to a use of these Ig binding proteins or affinity matrices for affinity purification of immunoglobulins and to methods of affinity purification using the Ig binding proteins of the invention.

21 Claims, 2 Drawing Sheets
Specification includes a Sequence Listing.

(56) References Cited

U.S. PATENT DOCUMENTS

| | | |
|---|---|---|
| 2007/0189963 A1 | 8/2007 | Neri et al. |
| 2007/0248536 A1 | 10/2007 | Fiedler et al. |
| 2007/0286843 A1 | 12/2007 | Pfizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0096276 A1* | 4/2013 | Yoshida .................. C07K 1/22 530/324 |
| 2013/0097737 A1 | 4/2013 | Kovalic et al. |
| 2013/0157878 A1 | 6/2013 | Kunert et al. |
| 2014/0135476 A1 | 5/2014 | Hall et al. |
| 2014/0219959 A1 | 8/2014 | Nerkamp et al. |
| 2015/0183846 A1 | 7/2015 | Lange et al. |
| 2018/0030098 A1 | 2/2018 | Bosse-Doenecke et al. |
| 2018/0030140 A1 | 2/2018 | Bosse-Doenecke et al. |
| 2018/0194819 A1 | 7/2018 | Fiedler et al. |
| 2018/0273636 A1 | 9/2018 | Settele et al. |
| 2018/0305463 A1 | 10/2018 | Haupts |
| 2019/0117791 A1 | 4/2019 | Haupts et al. |
| 2021/0179678 A1 | 6/2021 | Fiedler et al. |

FOREIGN PATENT DOCUMENTS

| | | | |
|---|---|---|---|
| EP | 2 532 672 A2 | 12/2012 | |
| EP | 2 727 942 A1 | 5/2014 | |
| EP | 2 738 180 | 6/2014 | |
| EP | 2829552 A1 | 1/2015 | |
| RU | 2134696 C1 | 8/1999 | |
| WO | WO 2005/044845 A2 | 5/2005 | |
| WO | WO 2007/054120 A1 | 5/2007 | |
| WO | WO 2012/171541 A1 | 12/2012 | |
| WO | WO 2013/186329 A1 | 12/2013 | |
| WO | WO 2014/094799 | 6/2014 | |
| WO | WO-2016079033 A1 * | 5/2016 | .......... C07K 16/065 |
| WO | WO 2016/124670 A1 | 8/2016 | |
| WO | WO 2016/124702 A1 | 8/2016 | |
| WO | WO 2017/013129 | 1/2017 | |
| WO | WO 2017/013136 | 1/2017 | |
| WO | WO 2017009421 | 1/2017 | |
| WO | WO 2018/029157 A1 | 2/2018 | |
| WO | WO 2019/030156 A1 | 2/2019 | |
| WO | WO 2019/152318 A1 | 8/2019 | |

OTHER PUBLICATIONS

Office Action corresponding to U.S. Appl. No. 16/376,847 dated Feb. 24, 2021.
Office Action corresponding to U.S. Appl. No. 15/548,976 dated Mar. 17, 2020.
Abedi et al. (1998) Green fluorescent protein as a scaffold for intracellular presentation of peptides. Nucleic Acids Research 26(2):623-630.
Advisory Action corresponding to U.S. Appl. No. 10/030,605 dated Oct. 13, 2006.
Advisory Action corresponding to U.S. Appl. No. 11/732,632 dated Jun. 30, 2010.
Advisory Action corresponding to U.S. Appl. No. 12/072,959 dated May 18, 2010.
Baker et al. (1994) Protein Expression Using Cotranslational Fusion and Cleavage of Ubiquitin. The Journal of Biological Chemistry 269(41):25381-25386.
Beal et al. (1996) Surface hydrophobic residues of multiubiquitin chains essential for proteolytic targeting. PNAS 93:861-866.
Beste et al. (1999) Small antibody-like proteins with prescribed ligand specificities derived from the lipocalin fold. PNAS 96:1898-1903.
Birchler et al. (1999) Selective targeting and photocoagulation of ocular angiogenesis mediated by a phage-derived human antibody fragment. Nature Biotechnology 17:984-988.
Bird et al. (1988) Single-Chain Antigen-Binding Proteins. Science. 242:423-426.
Bofill et al. (2005) Engineering Stabilising beta-Sheet Interactions into a Conformationally Flexible Region of the Folding Transition State of Ubiquitin. Journal of Molecular Biology 353(2):373-384.
Bolton et al. (2001) Structure and Properties of a Dimeric N-terminal Fragment of Human Ubiquitin. Journal of Molecular Biology 314(4):773-787.
Borsi et al. (2003) Selective targeted delivery of TNFα to tumor blood vessels. Blood 102(13):4384-4392.
Brinkmann et al. (1993) A recombinant immunotoxin containing a disulfide-stabilized Fv-fragment. PNAS 90:7538-7542.
Brinkmann et al. (1997) Stabilization of a Recombinant Fv Fragment by Base-Loop Interconnection and VH-VL Permutation. Journal of Molecular Biology 268:107-117.
Buchberger et al. (2001) The UBX Domain: A Widespread Ubiquitin-Like Module. Journal of Molecular Biology 307(1):17-24.
Burch & Haas (1994) Site-directed mutagenesis of ubiquitin. Differential roles for arginine in the interaction with ubiquitin-activating enzyme. Biochemistry 33(23):7300-7308.
Campion et al. (1990) Biochemical Properties of Site-Directed Mutants of Human Epidermal Growth Factor: Importance of Solvent-Exposed Hydrophobic Residues of the Amino-Terminal Domain in Receptor Binding. Biochemistry 29(42):9988-9993.
Connolly (1983) Solvent-Accessible Surfaces of Proteins and Nucleic Acids. Science 221(4612):709-713.
Corrected Notice of Allowability corresponding to U.S. Appl. No. 11/656,646 dated Sep. 26, 2013.
Database Geneseq online Aug. 18, 2011 (Aug. 18, 2011)Hetero-multimeric modified ubiquitin protein, SEQ ID 44. XP002756535, retrieved from EBI accession No. GSP:AZJ58575 Database accession No. AZJ58575.
Database Geneseq online Dec. 4, 2014 (Dec. 4, 2014)Anti-EGFR1 antibody light chain-TGF beta RII fusion protein, SEQ: 30., XP002756536, retrieved from EBI accession No. GSP:BBP24113 Database accession No. BBP24113.
Daugherty et al. (1998) Antibody affinity maturation using bacterial surface display. Protein Engineering 11(9):825-832.
De Kruif et al. (1995) Selection and Application of Human Single Chain Fv Antibody Fragments from a Semi-synthetic Phage Antibody Display Library with Designed CDR3 Regions. Journal of Molecular Biology 248:97-105.
Decision to Grant corresponding to Russian Patent Application No. 2012115491/10(023353) dated Nov. 20, 2014.
Deed of Grant corresponding to Australian Patent No. 2010332932 dated May 2, 2013.
Deed of Grant corresponding to Australian Patent No. 2010332938 dated Apr. 4, 2013.
Dikic et al. (2009) Ubiquitin-binding domains—from structures to functions. Nature Reviews 10:659-671.
Ebersbach et al. (2007) Affilin—Novel Binding Molecules Based on Human (-B-Crystallin, an All (-Sheet Protein. Journal of Molecular Biology 372:172-185.
Ecker et al. (1987) Gene Synthesis, Expression, Structures, and Functional Activities of Site-specific Mutants of Ubiquitin. The Journal of Biological Chemistry 262(29):14213-14221.
Ermolenko et al. (2003) Noncharged amino acid residues at the solvent-exposed positions in the middle and at the C terminus of the alpha-helix have the same helical propensity. Protein Science 12(6):1169-1176.
European Search Report corresponding to European Patent Application No. 06 118 519.5-2401 dated Apr. 2, 2007.
European Search Report corresponding to European Patent Application No. 09 176 574.3-2401 dated Jan. 18, 2010.
European Search Report corresponding to European Patent Application No. 10 181 802.9-2401 dated Feb. 10, 2011.
Fiedler et al. (2006) Affilintm Molecules: Novel Ligands for Bioseparation. Food and Bioproducts Processing. 84(C1):3-8.
Finucane et al. (1999a) Core-Directed Protein Design. I. An Experimental Method for Selecting Stable Proteins from Combinatorial Libraries. Biochemistry 38:11604-11612.

(56) References Cited

OTHER PUBLICATIONS

Finucane et al. (1999b) Core-Directed Protein Design. II. Rescue of a Multiply Mutated and Destabilized Variant of Ubiquitin. Biochemistry 38(36):11613-11623.
Friedman et al. (2009) Engineering and characterization of a bispecific HER2 X EGFR-binding affibody molecule. Biotechnology and applied biochemistry academic press US 54(2): 121-131.
Gebauer & Skerra (2009) Engineered protein scaffolds as next-generation antibody therapeutics. Current Opinion in Chemical Biology 13(3):245-255.
Grabulovski et al. (2007) A Novel, Non-immunogenic Fyn SH3-derived Binding Protein with Tumor Vascular Targeting Properties. The Journal of Biological Chemistry 282(5):3196-3204.
Guo et al. (2004) Protein tolerance to random amino acid change. PNAS 101(25):9205-9210.
Hanes & Plückthun (1997) In vitro selection and evolution of functional proteins by using ribosome display. PNAS 94(10):4937-4942.
Hanes et al. (1998) Ribosome display efficiently selects and evolves high-affinity antibodies in vitro from immune libraries. PNAS 95:14130-14135.
Hanes et al. (2000) Picomolar affinity antibodies from a fully synthetic naive library selected and evolved by ribosome display. Nature Biotechnology 18:1287-1292.
He & Taussig (1997) Antibody-ribosome-mRNA (ARM) complexes as efficient selection particles for in vitro display and evolution of antibody combining sites. Nucleic Acids Research 25(24):5132-5134.
Hershko & Ciechanover (1998) The Ubiquitin System. Annu Rev Biochem 67:425-479.
Hey et al. (2005) Artificial, non-antibody binding proteins for pharmaceutical and industrial applications. TRENDS in Biotechnology 23(10):514-522.
Humphrey et al. (1990) Anti-synthetic peptide antibody reacting at the fusion junction of deletion—mutant epidermal growth factor receptors in human glioblastoma. Proc Natl Acad Sci. 87:4207-4211.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability (Chapter I of the Patent Cooperation Treaty) corresponding to International Patent Application No. PCT/EP2016/052345 dated Aug. 8, 2017.
International Preliminary Report on Patentability corresponding to International Patent Application No. PCT/EP2004/005730 dated May 13, 2005.
International Preliminary Report on Patentability corresponding to International Patent Application No. PCT/EP2016/067216 dated Jan. 23, 2018.
International Search Report and Written Opinion corresponding to International Application No. PCT/EP2016/066774 dated Sep. 14, 2016.
International Search Report and Written Opinion corresponding to International Application No. PCT/EP2016/067216 dated Oct. 12, 2016.
International Search Report and Written Opinion corresponding to International Patent Application No. PCT/EP2016/052408 dated May 2, 2016.
International Search Report corresponding to International Application No. PCT/EP2016/067207 dated Sep. 29, 2016.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2011/002962 dated Mar. 19, 2012.
International Search Report corresponding to International Patent Application No. PCT/EP2012/061455 dated Oct. 25, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
Interview Summary and Corrected Notice of Allowability corresponding to U.S. Appl. No. 11/283,332 dated Jul. 1, 2014.
Interview Summary and Corrected Notice of Allowability corresponding to U.S. Appl. No. 12/072,959 dated Jun. 27, 2014.
Interview Summary correponding to U.S. Appl. No. 11/283,332 dated Dec. 13, 2013.
Jackson (2006) Ubiquitin: a small protein folding paradigm. Org Biomol Chem 4(10):1845-1853.
Khorasanizadeh et al. (1993) Folding and stability of a tryptophan-containing mutant of ubiquitin. Biochemistry 32(27):7054-7063.
Kiel & Serrano (2006) The Ubiquitin Domain Superfold: Structure-based Sequence Alignments and Characterization of Binding Epitopes. Journal of Molecular Biology 355(4):821-844.
Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.
Koide et al. (1998)The Fibronectin Type III Domain as a Scaffold for Novel Binding Proteins. Journal of Molecular Biology 284:1141-1151.
Kolchanov & Shindyalov (1988) Single amino acid substitutions producing instability of globular proteins. Calculation of their frequencies in the entire mutational spectra of the alpha- and beta-subunits of human hemoglobin. Journal of Molecular Evolution 27:154-162.
Krantz et al. (2004) Discerning the Structure and Energy of Multiple Transition States in Protein Folding using ψ-Analysis. Journal of Molecular Biology 337(2):463-475.
Krippner-Heidenreich et al. (2008) Single-chain TNF, a TNF derivative with enhanced stability and antitumoral activity. Journal of Immunology 180:8176-8183.
Ku & Schultz (1995) Alternate protein frameworks for molecular recognition. PNAS 92:6552-6556.
Larsen & Wang. (2002) The Ubiquitin Superfamily: Members, Features, and Phylogenies. Journal of Proteome Research 1:411-419.
Laub et al. (1995) Localized solution structure refinement of an F45W variant of ubiquitin using stochastic boundary molecular dynamics and NMR distance restraints. Protein Science 4:973-982.
Lazar & Wang (1997) H.De novo design of the hydrophobic core of ubiquitin. Protein Science 6:1167-1178.
Lipovsek & Pluckthun (2004) In-vitro protein evolution by ribosome display and mRNA display. Journal of Immunological Methods 290:51-67.
Lo et al. (2009) Structural Basis for Recognition of Diubiquitins by NEMO. Molecular Cell 33:602-615.
Loladze et al. (2005) Both helical propensity and side-chain hydrophobicity at a partially exposed site in alpha-helix contribute to the thermodynamic stability of ubiquitin. Proteins 58(1):1-6.
Lorey et al. (2014) Novel ubiquitin-derived high affinity binding proteins with tumor targeting properties. Journal of Biological Chemistry. 289(12):8493-8507.
Mayr et al. (1994) Domain Interactions and Connecting Peptides in Lens Crystallins. Journal of Molecular Biology 235:84-88.
McConnell & Hoess (1995) Tendamistat as a Scaffold for Conformationally Constrained Phage Peptide Libraries. The Journal of Molecular Biology 250:460-470.
Miura et al. (1999) Characterization of the Binding Interface between Ubiquitin and Class I Human Ubiquitin-conjugating Enzyme

(56) References Cited

OTHER PUBLICATIONS 2b by Multidimensional Heteronuclear NMR Spectroscopy in Solution Journal of Molecular Biology 290:213-228.
Müller & Skerra (1994) A.Grafting of a High-Affinity Zn(II)-Binding Site on the β-Barrel of Retional-Binding Protein Results in Enhanced Folding Stability and Enables Simplified Purification. Biochemistry 33(47):14126-14135.
Müller et al. (2001) SUMO, ubiquitin's mysterious cousin. Nat. Rev. Mol. Cell Biol 2:202-210.
Nord et al. (1997) Binding proteins selected from combinatorial libraries of an (-helical bacterial receptor domain. Nature Biotechnology 15:772-777.
Notice of Allowance corresponding to U.S. Appl. No. 10/030,605 dated Apr. 14, 2009.
Notice of Allowance corresponding to U.S. Appl. No. 11/283,332 dated Jun. 6, 2014.
Notice of Allowance corresponding to U.S. Appl. No. 11/656,646 dated Aug. 27, 2013.
Notice of Allowance corresponding to U.S. Appl. No. 11/732,632 dated Aug. 23, 2010.
Notice of Allowance corresponding to U.S. Appl. No. 12/072,959 dated Jun. 3, 2014.
Notice of Allowance corresponding to U.S. Appl. No. 12/514,550 dated Sep. 10, 2013.
Notice of Allowance corresponding to U.S. Appl. No. 13/142,195 dated Aug. 4, 2014.
Notice of Allowance corresponding to U.S. Appl. No. 13/144,809 dated Mar. 3, 2014.
Notice of Allowance corresponding to U.S. Appl. No. 14/126,358 dated Sep. 9, 2016.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification Concerning Transmittal of International Preliminary Report on Patentability (Chapter I of the Patent Cooperation Treaty) corresponding to International Patent Application No. PCT/EP2016/052345 dated Apr. 11, 2016.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Patent Application No. PCT/EP2005/010932 dated May 3, 2007.
Nygren & Uhlen (1997) Scaffolds for engineering novel binding sites in proteins. Current Opinion in Structural Biology 7:463-469.
Office Action (Restriction Requirement) corresponding to U.S. Appl. No. 15/549,022 dated May 3, 2018.
Office Action (Restriction Requirement) corresponding to U.S. Appl. No. 15/549,022 dated Nov. 8, 2018.
Office Action corresponding to Australian Patent Application No. 2012268970 dated Aug. 27, 2015.
Office Action corresponding to Canadian Patent Application No. 2,778,871 dated Jan. 30, 2014.
Office Action corresponding to Canadian Patent Application No. 2,837,804 dated May 1, 2015.
Office Action corresponding to Chinese Patent Application No. 201080056911.6 dated Jul. 31, 2013. Translation.
Office Action corresponding to European Patent Application No. 00 944 034.8-2401 dated Oct. 7, 2004.
Office action corresponding to European Patent Application No. EP 10 787 815.9-1410 dated Aug. 13, 2013.
Office Action corresponding to Japanese Patent Application No. 2012-504036 dated Aug. 26, 2013.
Office Action corresponding to Japanese Patent Application No. 2012-542583 dated Apr. 22, 2014.
Office Action corresponding to Korean Patent Application No. 10-2011-7018847 dated Jan. 30, 2013. Translation.
Office Action corresponding to Russian Patent Application No. 2012114662/10(022146) dated Dec. 18, 2013.
Office Action corresponding to Russian Patent Application No. 2012114662/10(022146) dated Sep. 8, 2014. (with Traslation).
Office Action corresponding to Russian Patent Application No. 2012115491 dated Dec. 24, 2013.
Office Action corresponding to U.S. Appl. No. 10/030,605 dated Apr. 12, 2006.
Office Action corresponding to U.S. Appl. No. 10/030,605 dated Aug. 10, 2005.
Office Action corresponding to U.S. Appl. No. 10/030,605 dated Feb. 15, 2005.
Office Action corresponding to U.S. Appl. No. 10/030,605 dated Feb. 28, 2007.
Office Action corresponding to U.S. Appl. No. 10/030,605 dated Jul. 1, 2008.
Office Action corresponding to U.S. Appl. No. 10/030,605 dated Nov. 16, 2007.
Office Action corresponding to U.S. Appl. No. 10/030,605 dated Sep. 21, 2004.
Office Action corresponding to U.S. Appl. No. 11/283,332 dated Jan. 9, 2008.
Office Action corresponding to U.S. Appl. No. 11/283,332 dated Mar. 3, 2010.
Office Action corresponding to U.S. Appl. No. 11/283,332 dated May 30, 2008.
Office Action corresponding to U.S. Appl. No. 11/283,332 dated Nov. 28, 2008.
Office Action corresponding to U.S. Appl. No. 11/283,332 dated Sep. 3, 2013.
Office Action corresponding to U.S. Appl. No. 11/283,332 dated Sep. 4, 2009.
Office Action corresponding to U.S. Appl. No. 11/656,646 dated May 25, 2010.
Office Action corresponding to U.S. Appl. No. 11/656,646 dated Nov. 13, 2009.
Office Action corresponding to U.S. Appl. No. 11/656,646 dated Sep. 1, 2009.
Office Action corresponding to U.S. Appl. No. 11/732,632 dated Aug. 21, 2009.
Office Action corresponding to U.S. Appl. No. 11/732,632 dated Jun. 3, 2009.
Office Action corresponding to U.S. Appl. No. 11/732,632 dated Mar. 19, 2010.
Office Action corresponding to U.S. Appl. No. 12/072,959 dated Aug. 30, 2013.
Office Action corresponding to U.S. Appl. No. 12/072,959 dated Jan. 27, 2009.
Office Action corresponding to U.S. Appl. No. 12/072,959 dated Jan. 5, 2010.
Office Action corresponding to U.S. Appl. No. 12/072,959 dated Jul. 24, 2008.
Office Action corresponding to U.S. Appl. No. 12/514,550 dated Aug. 3, 2011.
Office Action corresponding to U.S. Appl. No. 12/514,550 dated Mar. 12, 2012.
Office Action corresponding to U.S. Appl. No. 12/514,550 dated Sep. 15, 2011.
Office Action corresponding to U.S. Appl. No. 13/142,195 dated Feb. 11, 2013.
Office Action corresponding to U.S. Appl. No. 13/142,195 dated Feb. 4, 2014.
Office Action corresponding to U.S. Appl. No. 13/142,195 dated May 29, 2013.
Office Action corresponding to U.S. Appl. No. 13/144,809 dated Oct. 18, 2013.
Office Action corresponding to U.S. Appl. No. 13/516,002 dated Apr. 6, 2015.

(56) References Cited

OTHER PUBLICATIONS

Office Action corresponding to U.S. Appl. No. 13/516,002 dated Jan. 26, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 6, 2016.
Office Action corresponding to U.S. Appl. No. 14/407,213 dated May 25, 2016.
Office Action corresponding to U.S. Appl. No. 15/744,054 dated Mar. 14, 2019.
Office Action Restriction Requirement corresponding to U.S. Appl. No. 14/126,358 dated Oct. 28, 2015.
Office Action Restriction Requirement corresponding to U.S. Appl. No. 14/407,213 dated Jan. 21, 2016.
Office Action Restriction Requirement corresponding to U.S. Appl. No. 15/548,976 dated Jun. 14, 2019.
Office Action corresponding to U.S. Appl. No. 15/744,054 dated Jul. 30, 2019.
Ohashi et al. (2007) Efficient protein selection based on ribosome display system with purified components. Biochemical and Biophysical Research Communications 352:270-276.
Pack & Pluckthun (1992) A.Miniantibodies: Use of Amphipathic Helices to Produce Functional, Flexibly Linked Dimeric Fv Fragments with High Avidity in *Escherichia coli*. Biochemsitry 31(6):1579-1584.
Raasi Shahri et al. (2004) Binding of polyubiquitin chains to ubiquitin-associated (UBA) domains of HHR23A. J. Mol. Biol. 34:1367-1379.
Rahighi et al. (2009) Specific Recognition of Linear Ubiquitin Chains by NEMO Is Important for NF-kB Activation. Cell 136:1098-1109.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4): 167-187.
Skerra et al. (2007) Alternative non-antibody scaffolds for molecular recognition. Current Opinion in Biotechnology 18(4):295-304.
Smith et al. (1998) Small Binding Proteins Selected from a Conbinatorial Repertoire of Knottins Displayed on Phage. Journal of Molecular Biology 277(2):317-332.
Ubiquitin-like Superfamily (2004) pp. 1-4.
Weidle et al. (2013) The Emerging Role of New Protein Scaffold-based Agents for Treatment of Cancer. Caner Genomics & Proteomics 10(4):155-168.
Wells & Lowmann (1992).Rapid evolution of peptide and protein binding properties in vitro. Current Opinion in Biotechnology 3:355-362.
Wells (1990) Additivity of Mutational Effects in Proteins. Biochemistry 29(37):8509-8517.
Zahnd et al. (2007) Ribosome display: selecting and evolving proteins in vitro that specifically bind to a target. Nature Methods 4(3):269-279.
Zhang et al. (1997) Directed evolution of a fucosidase from a galactosidase by DNA shuffling and screening. PNAS 94:4504-4509.
Extended European Search Report corresponding to European Patent Application No. 18213661 .4-1111 dated May 31, 2019.
International Search Report corresponding to International Patent Application No. PCT/EP2019/085596 dated Feb. 6, 2020.
International Search Report corresponding to International Patent Application No. PCT/EP2020/052438 dated Mar. 19, 2020.
Written Opinion corresponding to International Application No. PCT/EP2019/085596 dated Jun. 25, 2020.
Written Opinion corresponding to International Application No. PCT/EP2020/052438 dated Aug. 6, 2020.

\* cited by examiner

FIG. 1. Alkaline stable Ig binding proteins
FIG. 1A. Preferred alkaline stable Ig binding proteins
FIG. 1B. Generic sequence of preferred alkaline stable artificial Ig binding proteins
FIG. 2. Alkaline stability of variants of IB14
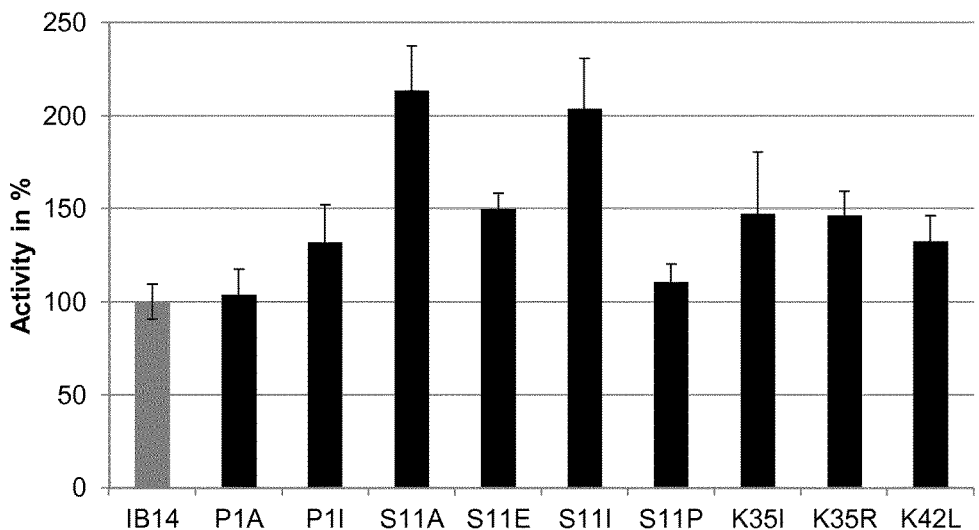

FIG. 3. cs14 with at least 1I, 11A, 35R
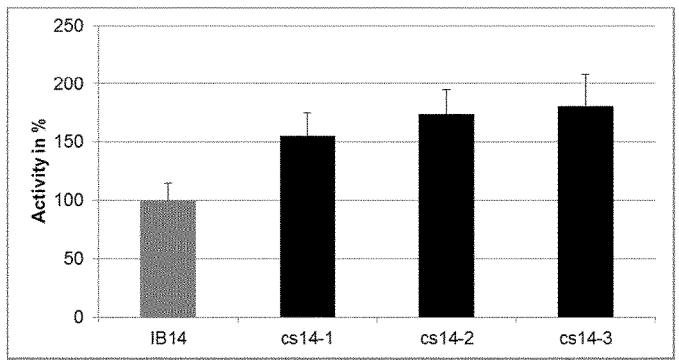
FIG. 4. cs27 with at least 1I, 11A, 35R
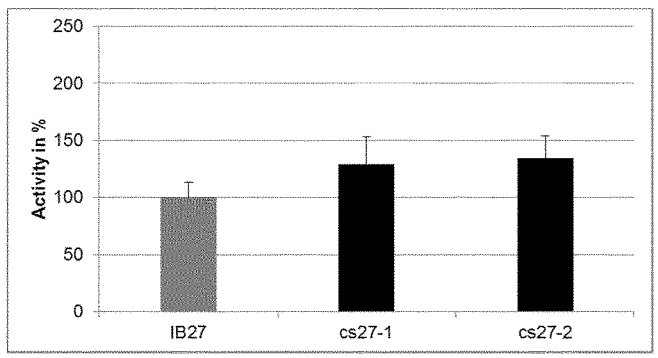
FIG. 5. Ig binding of cs14, cs25, cs74, and cs47
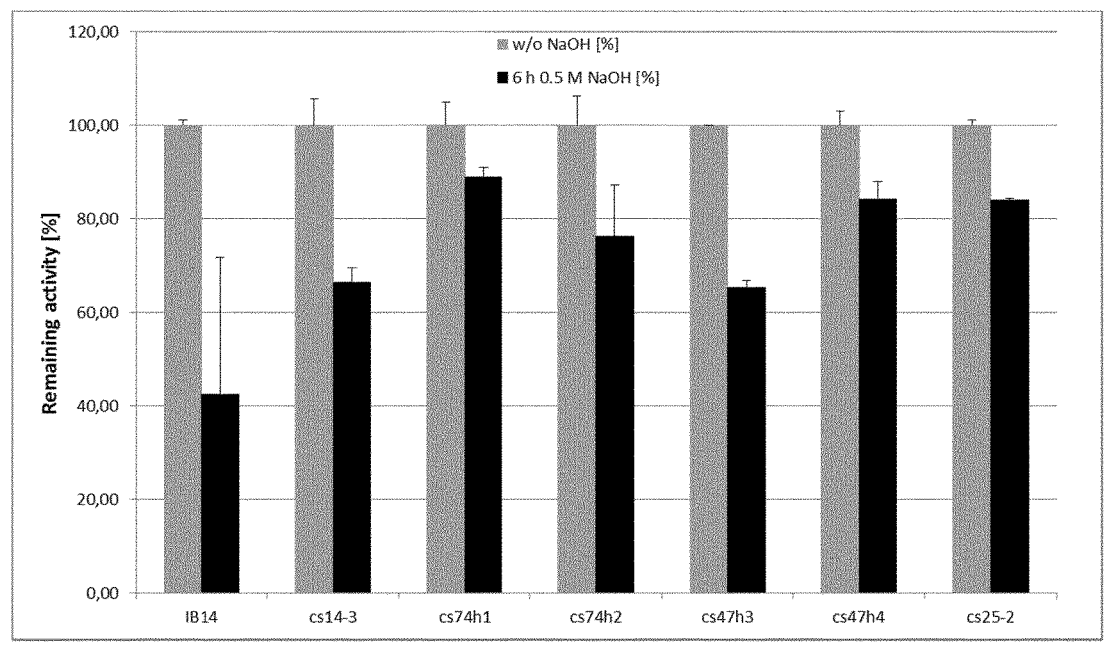

SEQUENCE LISTING

```
<160> NUMBER OF SEQ ID NOS: 61

<210> SEQ ID NO 1
<211> LENGTH: 58
<212> TYPE: PRT
<213> ORGANISM: Artificial Sequence
<220> FEATURE:
<223> OTHER INFORMATION: generic sequence 1
<220> FEATURE:
<221> NAME/KEY: variant
<222> LOCATION: (1)..(1)
<223> OTHER INFORMATION: may be replaced by V, N, Q, or P
<220> FEATURE:
<221> NAME/KEY: variant
<222> LOCATION: (2)..(2)
<223> OTHER INFORMATION: may be replaced by D or Q
<220> FEATURE:
<221> NAME/KEY: variant
<222> LOCATION: (3)..(3)
<223> OTHER INFORMATION: may be replaced by N or S
<220> FEATURE:
<221> NAME/KEY: variant
<222> LOCATION: (4)..(4)
<223> OTHER INFORMATION: may be replaced by  N
<220> FEATURE:
<221> NAME/KEY: variant
<222> LOCATION: (5)..(5)
<223> OTHER INFORMATION: may be replaced by F
<220> FEATURE:
<221> NAME/KEY: variant
<222> LOCATION: (6)..(6)
<223> OTHER INFORMATION: may be replaced by N, A, or S
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by E or A
<220> FEATURE:
<221> NAME/KEY: variant
<222> LOCATION: (11)..(11)
<223> OTHER INFORMATION: may be replaced by N
<220> FEATURE:
<221> NAME/KEY: variant
<222> LOCATION: (15)..(15)
<223> OTHER INFORMATION: may be replaced by Q
<220> FEATURE:
<221> NAME/KEY: variant
<222> LOCATION: (16)..(16)
<223> OTHER INFORMATION: may be replaced by V
<220> FEATURE:
<221> NAME/KEY: variant
<222> LOCATION: (18)..(18)
```

```
<223> OTHER INFORMATION: may be replaced by N
<220> FEATURE:
<221> NAME/KEY: variant
<222> LOCATION: (19)..(19)
<223> OTHER INFORMATION: may be replaced by M
<220> FEATURE:
<221> NAME/KEY: variant
<222> LOCATION: (21)..(21)
<223> OTHER INFORMATION: may be replaced by S or D
<220> FEATURE:
<221> NAME/KEY: variant
<222> LOCATION: (23)..(23)
<223> OTHER INFORMATION: may be replaced by N
<220> FEATURE:
<221> NAME/KEY: variant
<222> LOCATION: (24)..(24)
<223> OTHER INFORMATION: may be replaced by A
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (28)..(28)
<223> OTHER INFORMATION: may be replaced by S or A
<220> FEATURE:
<221> NAME/KEY: variant
<222> LOCATION: (29)..(29)
<223> OTHER INFORMATION: may be replaced by G
<220> FEATURE:
<221> NAME/KEY: variant
<222> LOCATION: (40)..(40)
<223> OTHER INFORMATION: may be replaced by Q or T
<220> FEATURE:
<221> NAME/KEY: variant
<222> LOCATION: (42)..(42)
<223> OTHER INFORMATION: may be replaced by A or T
<220> FEATURE:
<221> NAME/KEY: variant
<222> LOCATION: (43)..(43)
<223> OTHER INFORMATION: may be replaced by N or S
<220> FEATURE:
<221> NAME/KEY: variant
<222> LOCATION: (44)..(44)
<223> OTHER INFORMATION: may be replaced by V or L
<220> FEATURE:
<221> NAME/KEY: variant
<222> LOCATION: (46)..(46)
<223> OTHER INFORMATION: may be replaced by A
<220> FEATURE:
<221> NAME/KEY: variant
<222> LOCATION: (49)..(49)
<223> OTHER INFORMATION: may be replaced by Q
<220> FEATURE:
<221> NAME/KEY: variant
<222> LOCATION: (52)..(52)
<223> OTHER INFORMATION: may be replaced by D or S
<220> FEATURE:
<221> NAME/KEY: variant
<222> LOCATION: (53)..(53)
<223> OTHER INFORMATION: may be replaced by E
<220> FEATURE:
<221> NAME/KEY: variant
<222> LOCATION: (54)..(54)
<223> OTHER INFORMATION: may be replaced by S
<220> FEATURE:
<221> NAME/KEY: variant
<222> LOCATION: (58)..(58)
<223> OTHER INFORMATION: may be replaced by K

<400> SEQUENCE: 1

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
```

```
                    35                  40                  45

Lys Lys Leu Asn Asp Ala Gln Ala Pro Pro
    50                  55

<210> SEQ ID NO 2
<211> LENGTH: 58
<212> TYPE: PRT
<213> ORGANISM: Artificial Sequence
<220> FEATURE:
<223> OTHER INFORMATION: Generic sequence 2
<220> FEATURE:
<221> NAME/KEY: variant
<222> LOCATION: (1)..(1)
<223> OTHER INFORMATION: may be replaced by N or P
<220> FEATURE:
<221> NAME/KEY: variant
<222> LOCATION: (5)..(5)
<223> OTHER INFORMATION: may be replaced by F
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by E or A
<220> FEATURE:
<221> NAME/KEY: variant
<222> LOCATION: (11)..(11)
<223> OTHER INFORMATION: may be replaced by N
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (28)..(28)
<223> OTHER INFORMATION: may be replaced by S
<220> FEATURE:
<221> NAME/KEY: variant
<222> LOCATION: (44)..(44)
<223> OTHER INFORMATION: may be replaced by V
<220> FEATURE:
<221> NAME/KEY: variant
<222> LOCATION: (46)..(46)
<223> OTHER INFORMATION: may be replaced by A
<220> FEATURE:
<221> NAME/KEY: variant
<222> LOCATION: (49)..(49)
<223> OTHER INFORMATION: may be replaced by Q
<220> FEATURE:
<221> NAME/KEY: variant
<222> LOCATION: (54)..(54)
<223> OTHER INFORMATION: may be replaced by S
<220> FEATURE:
<221> NAME/KEY: variant
<222> LOCATION: (58)..(58)
<223> OTHER INFORMATION: may be replaced by K

<400> SEQUENCE: 2

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Lys Asp Asp Pro Ser Val Ser Lys Glu Ile Leu Gly Glu Ala
            35                  40                  45

Lys Lys Leu Asn Asp Ala Gln Ala Pro Pro
    50                  55

<210> SEQ ID NO 3
<211> LENGTH: 58
<212> TYPE: PRT
```

<213> ORGANISM: Artificial Sequence
<220> FEATURE:
<223> OTHER INFORMATION: parental protein IB14 1A/28N (IB14a)

<400> SEQUENCE: 3

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 4
<211> LENGTH: 58
<212> TYPE: PRT
<213> ORGANISM: Artificial Sequence
<220> FEATURE:
<223> OTHER INFORMATION: parental protein IB27 1A

<400> SEQUENCE: 4

Ala Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: domain C

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: domain B

<400> SEQUENCE: 6

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala

```
                    35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: domain Z

<400> SEQUENCE: 7

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: domain Z/2

<400> SEQUENCE: 8

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: IB14 1I

<400> SEQUENCE: 9

Ile Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 10
<211> LENGTH: 58
<212> TYPE: PRT
<213> ORGANISM: Artificial Sequence
<220> FEATURE:
<223> OTHER INFORMATION: IB14 1A/28S (IB14b)
```

```
<400> SEQUENCE: 10

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 11
<211> LENGTH: 58
<212> TYPE: PRT
<213> ORGANISM: Artificial Sequence
<220> FEATURE:
<223> OTHER INFORMATION: IB14 11A

<400> SEQUENCE: 11

Pro Ala Ala Lys His Asp Lys Asp Gln Gln Ala Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 12
<211> LENGTH: 58
<212> TYPE: PRT
<213> ORGANISM: Artificial Sequence
<220> FEATURE:
<223> OTHER INFORMATION: IB14 11E

<400> SEQUENCE: 12

Pro Ala Ala Lys His Asp Lys Asp Gln Gln Glu Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 13
<211> LENGTH: 58
<212> TYPE: PRT
<213> ORGANISM: Artificial Sequence
<220> FEATURE:
<223> OTHER INFORMATION: IB14 11I

<400> SEQUENCE: 13

Pro Ala Ala Lys His Asp Lys Asp Gln Gln Ile Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55
```

-continued

```
<210> SEQ ID NO 14
<211> LENGTH: 58
<212> TYPE: PRT
<213> ORGANISM: Artificial Sequence
<220> FEATURE:
<223> OTHER INFORMATION: IB14 1P 28S (IB14d)

<400> SEQUENCE: 14

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 15
<211> LENGTH: 58
<212> TYPE: PRT
<213> ORGANISM: Artificial Sequence
<220> FEATURE:
<223> OTHER INFORMATION: IB14 35R

<400> SEQUENCE: 15

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Arg Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 16
<211> LENGTH: 58
<212> TYPE: PRT
<213> ORGANISM: Artificial Sequence
<220> FEATURE:
<223> OTHER INFORMATION: IB14 35I

<400> SEQUENCE: 16

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Ile Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 17
<211> LENGTH: 58
<212> TYPE: PRT
<213> ORGANISM: Artificial Sequence
<220> FEATURE:
<223> OTHER INFORMATION: IB14 42L

<400> SEQUENCE: 17

Pro Ala Ala Lys His Asp Lys Asp Gln Gln Ser Ala Phe Tyr Glu Ile
1               5                   10                  15
```

```
Leu His Leu Pro Asn Leu Thr Glu Asp Gln Arg Ser Ala Phe Ile Gln
            20                  25                  30

Ser Leu Lys Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 18
<211> LENGTH: 58
<212> TYPE: PRT
<213> ORGANISM: Artificial Sequence
<220> FEATURE:
<223> OTHER INFORMATION: alkaline stable Ig binding domain cs14-1 (IB14
      1I/11A/35R)

<400> SEQUENCE: 18

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Arg Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 19
<211> LENGTH: 58
<212> TYPE: PRT
<213> ORGANISM: Artificial Sequence
<220> FEATURE:
<223> OTHER INFORMATION: alkaline stable Ig binding domain cs14-2 (IB14
      1I/11A/35R/42L)

<400> SEQUENCE: 19

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 20
<211> LENGTH: 58
<212> TYPE: PRT
<213> ORGANISM: Artificial Sequence
<220> FEATURE:
<223> OTHER INFORMATION: alkaline stable Ig binding domain cs14-3
      (1I/11A/28N/35R/42L)

<400> SEQUENCE: 20

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55
```

<210> SEQ ID NO 21
<211> LENGTH: 58
<212> TYPE: PRT
<213> ORGANISM: Artificial Sequence
<220> FEATURE:
<223> OTHER INFORMATION: IB14 1P/28N (IB14c)

<400> SEQUENCE: 21

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 22
<211> LENGTH: 58
<212> TYPE: PRT
<213> ORGANISM: Artificial Sequence
<220> FEATURE:
<223> OTHER INFORMATION: IB27 1N

<400> SEQUENCE: 22

Asn Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 23
<211> LENGTH: 53
<212> TYPE: PRT
<213> ORGANISM: Artificial Sequence
<220> FEATURE:
<223> OTHER INFORMATION: cs27 delNC

<400> SEQUENCE: 23

Lys Phe Asp Glu Ala Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Val Leu Gly Glu Ala Gln Lys Leu
        35                  40                  45

Asn Asp Ser Gln Ala
    50

<210> SEQ ID NO 24
<211> LENGTH: 55
<212> TYPE: PRT
<213> ORGANISM: Artificial Sequence
<220> FEATURE:
<223> OTHER INFORMATION: cs27 delN

<400> SEQUENCE: 24

Ala Phe Asp Glu Ala Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Val Leu Gly Glu Ala Gln Lys Leu
        35                  40                  45

Asn Asp Ser Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: parental protein IB25 1A

<400> SEQUENCE: 25

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: alkaline stable Ig binding domain cs25 (IB25
      1I/11A/35R/42L)

<400> SEQUENCE: 26

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 27
<211> LENGTH: 318
<212> TYPE: PRT
<213> ORGANISM: Artificial Sequence
<220> FEATURE:
<223> OTHER INFORMATION: cs17 delNC hexamer

<400> SEQUENCE: 27

Lys Phe Asp Glu Ala Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Val Leu Gly Glu Ala Gln Lys Leu
        35                  40                  45

Asn Asp Ser Gln Ala Lys Phe Asp Glu Ala Gln Gln Ala Ala Phe Tyr
    50                  55                  60

Glu Ile Leu His Leu Pro Asn Leu Thr Glu Glu Gln Arg Asn Ala Phe
65                  70                  75                  80

```
Ile Gln Ser Leu Arg Asp Asp Pro Ser Val Ser Leu Glu Val Leu Gly
                85                  90                  95

Glu Ala Gln Lys Leu Asn Asp Ser Gln Ala Lys Phe Asp Glu Ala Gln
            100                 105                 110

Gln Ala Ala Phe Tyr Glu Ile Leu His Leu Pro Asn Leu Thr Glu Glu
            115                 120                 125

Gln Arg Asn Ala Phe Ile Gln Ser Leu Arg Asp Asp Pro Ser Val Ser
130                 135                 140

Leu Glu Val Leu Gly Glu Ala Gln Lys Leu Asn Asp Ser Gln Ala Lys
145                 150                 155                 160

Phe Asp Glu Ala Gln Gln Ala Ala Phe Tyr Glu Ile Leu His Leu Pro
                165                 170                 175

Asn Leu Thr Glu Glu Gln Arg Asn Ala Phe Ile Gln Ser Leu Arg Asp
            180                 185                 190

Asp Pro Ser Val Ser Leu Glu Val Leu Gly Glu Ala Gln Lys Leu Asn
            195                 200                 205

Asp Ser Gln Ala Lys Phe Asp Glu Ala Gln Gln Ala Ala Phe Tyr Glu
210                 215                 220

Ile Leu His Leu Pro Asn Leu Thr Glu Glu Gln Arg Asn Ala Phe Ile
225                 230                 235                 240

Gln Ser Leu Arg Asp Asp Pro Ser Val Ser Leu Glu Val Leu Gly Glu
                245                 250                 255

Ala Gln Lys Leu Asn Asp Ser Gln Ala Lys Phe Asp Glu Ala Gln Gln
            260                 265                 270

Ala Ala Phe Tyr Glu Ile Leu His Leu Pro Asn Leu Thr Glu Glu Gln
            275                 280                 285

Arg Asn Ala Phe Ile Gln Ser Leu Arg Asp Asp Pro Ser Val Ser Leu
290                 295                 300

Glu Val Leu Gly Glu Ala Gln Lys Leu Asn Asp Ser Gln Ala
305                 310                 315

<210> SEQ ID NO 28
<211> LENGTH: 290
<212> TYPE: PRT
<213> ORGANISM: Artificial Sequence
<220> FEATURE:
<223> OTHER INFORMATION: cs27 pentamer

<400> SEQUENCE: 28

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
            35                  40                  45

Gln Lys Leu Asn Asp Ser Gln Ala Pro Lys Ile Ala Ala Lys Phe Asp
50                  55                  60

Glu Ala Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Val Leu Gly Glu Ala Gln Lys Leu Asn Asp Ser
            100                 105                 110

Gln Ala Pro Lys Ile Ala Ala Lys Phe Asp Glu Ala Gln Gln Ala Ala
            115                 120                 125
```

```
Phe Tyr Glu Ile Leu His Leu Pro Asn Leu Thr Glu Glu Gln Arg Asn
        130                 135                 140

Ala Phe Ile Gln Ser Leu Arg Asp Asp Pro Ser Val Ser Leu Glu Val
145                 150                 155                 160

Leu Gly Glu Ala Gln Lys Leu Asn Asp Ser Gln Ala Pro Lys Ile Ala
                165                 170                 175

Ala Lys Phe Asp Glu Ala Gln Gln Ala Ala Phe Tyr Glu Ile Leu His
            180                 185                 190

Leu Pro Asn Leu Thr Glu Glu Gln Arg Asn Ala Phe Ile Gln Ser Leu
        195                 200                 205

Arg Asp Asp Pro Ser Val Ser Leu Glu Val Leu Gly Glu Ala Gln Lys
    210                 215                 220

Leu Asn Asp Ser Gln Ala Pro Lys Ile Ala Ala Lys Phe Asp Glu Ala
225                 230                 235                 240

Gln Gln Ala Ala Phe Tyr Glu Ile Leu His Leu Pro Asn Leu Thr Glu
                245                 250                 255

Glu Gln Arg Asn Ala Phe Ile Gln Ser Leu Arg Asp Asp Pro Ser Val
            260                 265                 270

Ser Leu Glu Val Leu Gly Glu Ala Gln Lys Leu Asn Asp Ser Gln Ala
        275                 280                 285

Pro Lys
    290

<210> SEQ ID NO 29
<211> LENGTH: 58
<212> TYPE: PRT
<213> ORGANISM: Artificial Sequence
<220> FEATURE:
<223> OTHER INFORMATION: alkaline stable Ig binding domain cs27-1 (IB27
      1I/11A/35R)

<400> SEQUENCE: 29

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: alkaline stable Ig binding domain cs27-2 (IB27
      I/11A/35R/42L)

<400> SEQUENCE: 30

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55
```

<210> SEQ ID NO 31
<211> LENGTH: 58
<212> TYPE: PRT
<213> ORGANISM: Artificial Sequence
<220> FEATURE:
<223> OTHER INFORMATION: alkaline stable Ig binding domain C 1I/11A/35R

<400> SEQUENCE: 31

Ile Asp Asn Lys Phe Asn Lys Glu Gln Gln Ala Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Arg Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: alkaline stable Ig binding domain C
      1I/11A/35R/42L

<400> SEQUENCE: 32

Ile Asp Asn Lys Phe Asn Lys Glu Gln Gln Ala Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: alkaline stable Ig binding domain B 1I/11A/35R

<400> SEQUENCE: 33

Ile Asp Asn Lys Phe Asn Lys Glu Gln Gln Ala Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 34
<211> LENGTH: 58
<212> TYPE: PRT
<213> ORGANISM: Artificial Sequence
<220> FEATURE:
<223> OTHER INFORMATION: alkaline stable Ig binding domain B
      1I/11A/35R/42L

<400> SEQUENCE: 34

Ile Asp Asn Lys Phe Asn Lys Glu Gln Gln Ala Ala Phe Tyr Glu Ile

```
                1               5                   10                  15
Leu His Leu Pro Asn Leu Asn Glu Glu Gln Arg Asn Gly Phe Ile Gln
            20                  25                  30

Ser Leu Arg Asp Asp Pro Ser Gln Ser Leu Asn Leu Leu Ala Glu Ala
        35                  40                  45

Lys Lys Leu Asn Asp Ala Gln Ala Pro Lys
        50                  55
```

<210> SEQ ID NO 35
<211> LENGTH: 58
<212> TYPE: PRT
<213> ORGANISM: Artificial Sequence
<220> FEATURE:
<223> OTHER INFORMATION: alkaline stable Ig binding domain  Z 1I/11A/35R

<400> SEQUENCE: 35

```
Ile Asp Asn Lys Phe Asn Lys Glu Gln Gln Ala Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 36
<211> LENGTH: 58
<212> TYPE: PRT
<213> ORGANISM: Artificial Sequence
<220> FEATURE:
<223> OTHER INFORMATION: alkaline stable Ig binding domain  Z 1I/11A/35R/42L

<400> SEQUENCE: 36

```
Ile Asp Asn Lys Phe Asn Lys Glu Gln Gln Ala Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Arg Asp Asp Pro Ser Gln Ser Leu Asn Leu Leu Ala Glu Ala
        35                  40                  45

Lys Lys Leu Asn Asp Ala Gln Ala Pro Lys
        50                  55
```

<210> SEQ ID NO 37
<211> LENGTH: 58
<212> TYPE: PRT
<213> ORGANISM: Artificial Sequence
<220> FEATURE:
<223> OTHER INFORMATION: alkaline stable Ig binding domain domain Z/2 1I/11A/35R

<400> SEQUENCE: 37

```
Ile Asp Ala Lys Phe Asp Lys Glu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Ala Leu Leu Ala Glu Ala
        35                  40                  45

Lys Lys Leu Asn Asp Ala Gln Ala Pro Lys
        50                  55
```

<210> SEQ ID NO 38
<211> LENGTH: 58
<212> TYPE: PRT
<213> ORGANISM: Artificial Sequence
<220> FEATURE:
<223> OTHER INFORMATION: alkaline stable Ig binding domain Z/2
      1I/11A/35R/42L

<400> SEQUENCE: 38

Ile Asp Ala Lys Phe Asp Lys Glu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Asn Leu Leu Ala Glu Ala
        35                  40                  45

Lys Lys Leu Asn Asp Ala Gln Ala Pro Lys
    50                  55

<210> SEQ ID NO 39
<211> LENGTH: 79
<212> TYPE: PRT
<213> ORGANISM: Artificial Sequence
<220> FEATURE:
<223> OTHER INFORMATION: alkaline stable Ig binding domain cs14-3 with
      coupling sequence and strep tag

<400> SEQUENCE: 39

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro Ala Ser Pro Ala Pro Ser
    50                  55                  60

Ala Pro Ser Ala Cys Ala Ser Trp Ser His Pro Gln Phe Glu Lys
65                  70                  75

<210> SEQ ID NO 40
<211> LENGTH: 79
<212> TYPE: PRT
<213> ORGANISM: Artificial Sequence
<220> FEATURE:
<223> OTHER INFORMATION: alkaline stable Ig binding domain cs27-2 with
      coupling sequence and strep tag

<400> SEQUENCE: 40

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys Ala Ser Pro Ala Pro Ser
    50                  55                  60

Ala Pro Ser Ala Cys Ala Ser Trp Ser His Pro Gln Phe Glu Lys
65                  70                  75

<210> SEQ ID NO 41
<211> LENGTH: 13
<212> TYPE: PRT

<213> ORGANISM: Artificial Sequence
<220> FEATURE:
<223> OTHER INFORMATION: coupling sequence

<400> SEQUENCE: 41

Ala Ser Pro Ala Pro Ser Ala Pro Ser Ala Cys Ala Ser
1               5                   10

<210> SEQ ID NO 42
<211> LENGTH: 58
<212> TYPE: PRT
<213> ORGANISM: Artificial Sequence
<220> FEATURE:
<223> OTHER INFORMATION: alkaline stable Ig binding domain cs74h1-2

<400> SEQUENCE: 42

Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 43
<211> LENGTH: 58
<212> TYPE: PRT
<213> ORGANISM: Artificial Sequence
<220> FEATURE:
<223> OTHER INFORMATION: alkaline stable Ig binding domain cs74h2-2

<400> SEQUENCE: 43

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 44
<211> LENGTH: 58
<212> TYPE: PRT
<213> ORGANISM: Artificial Sequence
<220> FEATURE:
<223> OTHER INFORMATION: alkaline stable Ig binding domain cs47h3-2

<400> SEQUENCE: 44

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 45
<211> LENGTH: 58
<212> TYPE: PRT

<213> ORGANISM: Artificial Sequence
<220> FEATURE:
<223> OTHER INFORMATION: alkaline stable Ig binding domain cs47h4-2

<400> SEQUENCE: 45

```
Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55
```

<210> SEQ ID NO 46
<211> LENGTH: 8
<212> TYPE: PRT
<213> ORGANISM: Artificial Sequence
<220> FEATURE:
<223> OTHER INFORMATION: StrepTag

<400> SEQUENCE: 46

```
Trp Ser His Pro Gln Phe Glu Lys
1               5
```

<210> SEQ ID NO 47
<211> LENGTH: 58
<212> TYPE: PRT
<213> ORGANISM: Artificial Sequence
<220> FEATURE:
<223> OTHER INFORMATION: parental protein IB74h1

<400> SEQUENCE: 47

```
Ala Ala Ala Lys Phe Asp Glu Ala Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55
```

<210> SEQ ID NO 48
<211> LENGTH: 58
<212> TYPE: PRT
<213> ORGANISM: Artificial Sequence
<220> FEATURE:
<223> OTHER INFORMATION: parental protein IB74h2

<400> SEQUENCE: 48

```
Ala Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55
```

<210> SEQ ID NO 49
<211> LENGTH: 58
<212> TYPE: PRT

```
<213> ORGANISM: Artificial Sequence
<220> FEATURE:
<223> OTHER INFORMATION: parental protein IB47h3

<400> SEQUENCE: 49

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 50
<211> LENGTH: 58
<212> TYPE: PRT
<213> ORGANISM: Artificial Sequence
<220> FEATURE:
<223> OTHER INFORMATION: parental protein IB47h4

<400> SEQUENCE: 50

Ala Ala Ala Lys His Asp Lys Asp Gln Gln Ser Ala Phe Tyr Glu Ile
1               5                   10                  15

Leu His Leu Pro Asn Leu Thr Glu Gly Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 51
<211> LENGTH: 58
<212> TYPE: PRT
<213> ORGANISM: Artificial Sequence
<220> FEATURE:
<223> OTHER INFORMATION: generic sequence including IB14 and IB27
<220> FEATURE:
<221> NAME/KEY: variant
<222> LOCATION: (1)..(1)
<223> OTHER INFORMATION: may be replaced by N or P
<220> FEATURE:
<221> NAME/KEY: variant
<222> LOCATION: (5)..(5)
<223> OTHER INFORMATION: may be replaced by F
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by A
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (28)..(28)
<223> OTHER INFORMATION: may be replaced by S
<220> FEATURE:
<221> NAME/KEY: variant
<222> LOCATION: (44)..(44)
<223> OTHER INFORMATION: may be replaced by V
<220> FEATURE:
<221> NAME/KEY: variant
<222> LOCATION: (49)..(49)
<223> OTHER INFORMATION: may be replaced by Q
```

```
<220> FEATURE:
<221> NAME/KEY: variant
<222> LOCATION: (54)..(54)
<223> OTHER INFORMATION: may be replaced by S
<220> FEATURE:
<221> NAME/KEY: variant
<222> LOCATION: (58)..(58)
<223> OTHER INFORMATION: may be replaced by K

<400> SEQUENCE: 51

Ala Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
        50                  55

<210> SEQ ID NO 52
<211> LENGTH: 58
<212> TYPE: PRT
<213> ORGANISM: Artificial Sequence
<220> FEATURE:
<223> OTHER INFORMATION: Generic sequence of preferred alkaline stable
      artifical IgG binding proteins
<220> FEATURE:
<221> NAME/KEY: variant
<222> LOCATION: (5)..(5)
<223> OTHER INFORMATION: may be replaced by F
<220> FEATURE:
<221> NAME/KEY: variant
<222> LOCATION: (7)..(7)
<223> OTHER INFORMATION: may be replaced by E
<220> FEATURE:
<221> NAME/KEY: variant
<222> LOCATION: (8)..(8)
<223> OTHER INFORMATION: may be replaced by A or E
<220> FEATURE:
<221> NAME/KEY: variant
<222> LOCATION: (25)..(25)
<223> OTHER INFORMATION: may be replaced by E
<220> FEATURE:
<221> NAME/KEY: variant
<222> LOCATION: (28)..(28)
<223> OTHER INFORMATION: may be replaced by S
<220> FEATURE:
<221> NAME/KEY: variant
<222> LOCATION: (42)..(42)
<223> OTHER INFORMATION: may be replaced by L
<220> FEATURE:
<221> NAME/KEY: variant
<222> LOCATION: (44)..(44)
<223> OTHER INFORMATION: may be replaced by V
<220> FEATURE:
<221> NAME/KEY: variant
<222> LOCATION: (46)..(46)
<223> OTHER INFORMATION: may be replaced by A
<220> FEATURE:
<221> NAME/KEY: variant
<222> LOCATION: (49)..(49)
<223> OTHER INFORMATION: may be replaced by Q
<220> FEATURE:
<221> NAME/KEY: variant
<222> LOCATION: (54)..(54)
<223> OTHER INFORMATION: may be replaced by S
<220> FEATURE:
<221> NAME/KEY: variant
<222> LOCATION: (58)..(58)
<223> OTHER INFORMATION: may be replaced by K

<400> SEQUENCE: 52

Ile Ala Ala Lys His Asp Lys Asp Gln Gln Ala Ala Phe Tyr Glu Ile
```

```
1               5                   10                  15
Leu His Leu Pro Asn Leu Thr Glu Asp Gln Arg Asn Ala Phe Ile Gln
            20                  25                  30

Ser Leu Arg Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 53
<211> LENGTH: 58
<212> TYPE: PRT
<213> ORGANISM: Artificial Sequence
<220> FEATURE:
<223> OTHER INFORMATION: cs27 46C

<400> SEQUENCE: 53

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Cys Glu Ala
        35                  40                  45

Gln Lys Leu Asn Asp Ser Gln Ala Pro Lys
    50                  55

<210> SEQ ID NO 54
<211> LENGTH: 58
<212> TYPE: PRT
<213> ORGANISM: Artificial Sequence
<220> FEATURE:
<223> OTHER INFORMATION: cs14 43C

<400> SEQUENCE: 54

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Cys Ile Leu Gly Glu Ala
        35                  40                  45

Lys Lys Leu Asn Asp Ala Gln Ala Pro Pro
    50                  55

<210> SEQ ID NO 55
<211> LENGTH: 174
<212> TYPE: PRT
<213> ORGANISM: Artificial Sequence
<220> FEATURE:
<223> OTHER INFORMATION: cs27 tetramer

<400> SEQUENCE: 55

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys Ile Ala Ala Lys Phe Asp
    50                  55                  60

Glu Ala Gln Gln Ala Ala Phe Tyr Glu Ile Leu His Leu Pro Asn Leu
65                  70                  75                  80
```

```
Thr Glu Glu Gln Arg Asn Ala Phe Ile Gln Ser Leu Arg Asp Asp Pro
                 85                  90                  95

Ser Val Ser Leu Glu Val Leu Gly Glu Ala Gln Lys Leu Asn Asp Ser
            100                 105                 110

Gln Ala Pro Lys Ile Ala Ala Lys Phe Asp Glu Ala Gln Gln Ala Ala
        115                 120                 125

Phe Tyr Glu Ile Leu His Leu Pro Asn Leu Thr Glu Glu Gln Arg Asn
    130                 135                 140

Ala Phe Ile Gln Ser Leu Arg Asp Asp Pro Ser Val Ser Leu Glu Val
145                 150                 155                 160

Leu Gly Glu Ala Gln Lys Leu Asn Asp Ser Gln Ala Pro Lys
                165                 170

<210> SEQ ID NO 56
<211> LENGTH: 58
<212> TYPE: PRT
<213> ORGANISM: Artificial Sequence
<220> FEATURE:
<223> OTHER INFORMATION: alkaline stable Ig binding domain cs25-1 (IB25
      1I/11A/35R)

<400> SEQUENCE: 56

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Arg Glu Ile Leu Ala Glu Ala
        35                  40                  45

Lys Lys Leu Asn Asp Ala Gln Ala Pro Lys
    50                  55

<210> SEQ ID NO 57
<211> LENGTH: 58
<212> TYPE: PRT
<213> ORGANISM: Artificial Sequence
<220> FEATURE:
<223> OTHER INFORMATION: alkaline stable Ig binding domain cs74h1-1

<400> SEQUENCE: 57

Ile Ala Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Arg Glu Ile Leu Gly Glu Ala
        35                  40                  45

Lys Lys Leu Asn Asp Ala Gln Ala Pro Pro
    50                  55

<210> SEQ ID NO 58
<211> LENGTH: 58
<212> TYPE: PRT
<213> ORGANISM: Artificial Sequence
<220> FEATURE:
<223> OTHER INFORMATION: alkaline stable Ig binding domain cs74h2-1

<400> SEQUENCE: 58

Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30
```

Ser Leu Arg Asp Asp Pro Ser Val Ser Arg Glu Ile Leu Gly Glu Ala
            35                  40                  45

Lys Lys Leu Asn Asp Ala Gln Ala Pro Pro
    50                  55

<210> SEQ ID NO 59
<211> LENGTH: 58
<212> TYPE: PRT
<213> ORGANISM: Artificial Sequence
<220> FEATURE:
<223> OTHER INFORMATION: alkaline stable Ig binding domain cs47h3-1

<400> SEQUENCE: 59

Ile Ala Ala Lys His Asp Lys Asp Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Arg Glu Val Leu Gly Glu Ala
            35                  40                  45

Gln Lys Leu Asn Asp Ser Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: alkaline stable Ig binding domain cs47h4-1

<400> SEQUENCE: 60

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Val Leu Gly Glu Ala
            35                  40                  45

Gln Lys Leu Asn Asp Ser Gln Ala Pro Lys
    50                  55

<210> SEQ ID NO 61
<211> LENGTH: 58
<212> TYPE: PRT
<213> ORGANISM: Artificial Sequence
<220> FEATURE:
<223> OTHER INFORMATION: alkaline stable Ig binding domain cs47h4-1
<220> FEATURE:
<221> NAME/KEY: MISC_FEATURE
<222> LOCATION: (5)..(5)
<223> OTHER INFORMATION: Xaa is Phe or His
<220> FEATURE:
<221> NAME/KEY: MISC_FEATURE
<222> LOCATION: (7)..(7)
<223> OTHER INFORMATION: Xaa is Glu or Lys
<220> FEATURE:
<221> NAME/KEY: MISC_FEATURE
<222> LOCATION: (8)..(8)
<223> OTHER INFORMATION: Xaa is Glu or Asp or Ala
<220> FEATURE:
<221> NAME/KEY: MISC_FEATURE
<222> LOCATION: (25)..(25)
<223> OTHER INFORMATION: Xaa is Glu or Asp
<220> FEATURE:
<221> NAME/KEY: MISC_FEATURE
<222> LOCATION: (28)..(28)
<223> OTHER INFORMATION: Xaa is Asn or Ser
<220> FEATURE:

-continued

```
<221> NAME/KEY: MISC_FEATURE
<222> LOCATION: (42)..(42)
<223> OTHER INFORMATION: Xaa is Leu or Lys
<220> FEATURE:
<221> NAME/KEY: MISC_FEATURE
<222> LOCATION: (44)..(44)
<223> OTHER INFORMATION: Xaa is Val or Ile
<220> FEATURE:
<221> NAME/KEY: MISC_FEATURE
<222> LOCATION: (46)..(46)
<223> OTHER INFORMATION: Xaa is Gly or Ala
<220> FEATURE:
<221> NAME/KEY: MISC_FEATURE
<222> LOCATION: (49)..(49)
<223> OTHER INFORMATION: Xaa is Gln or Lys
<220> FEATURE:
<221> NAME/KEY: MISC_FEATURE
<222> LOCATION: (54)..(54)
<223> OTHER INFORMATION: Xaa is Ser or Ala
<220> FEATURE:
<221> NAME/KEY: MISC_FEATURE
<222> LOCATION: (58)..(58)
<223> OTHER INFORMATION: Xaa is Pro or Lys

<400> SEQUENCE: 61

Ile Ala Ala Lys Xaa Asp Xaa Xaa Gln Gln Ala Ala Phe Tyr Glu Ile
1               5                   10                  15

Leu His Leu Pro Asn Leu Thr Glu Xaa Gln Arg Xaa Ala Phe Ile Gln
            20                  25                  30

Ser Leu Arg Asp Asp Pro Ser Val Ser Xaa Glu Xaa Leu Xaa Glu Ala
        35                  40                  45

Xaa Lys Leu Asn Asp Xaa Gln Ala Pro Xaa
    50                  55
```

ALKALINE STABLE IMMUNOGLOBULIN-BINDING PROTEINS

FIELD OF THE INVENTION

The present invention relates to alkaline stable immunoglobulin (Ig) binding proteins comprising one or more Ig binding domains with amino acids selected from the group consisting at least of 1I, 11A, 11E, 11I, 35R, 35I, and 42L. The invention further relates to affinity matrices comprising the alkaline stable Ig binding proteins of the invention. The invention also relates to a use of these Ig binding proteins or affinity matrices for affinity purification of immunoglobulins and to methods of affinity purification using the Ig binding proteins of the invention.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface Protein A from *Staphylococcus aureus* as selective ligand for immunoglobulins (see, for example, review by Huse et al., J. Biochem. Biophys. Methods 51, 2002: 217-231). Wild-type Protein A binds to the Fc region of IgG molecules with high affinity and selectivity and is stable at high temperatures and in a wide range of pH values. Variants of Protein A with improved properties such as alkaline stability are available for purifying antibodies and various chromatographic matrices comprising Protein A ligands are commercially available. However, in particular wild-type Protein A based chromatography matrices show a loss of binding capacity for immunoglobulins following exposure to alkaline conditions.

Technical Problems Underlying the Invention

Most large scale production processes for antibodies or Fc-containing fusion proteins use Protein A for affinity purification. However, due to limitations of Protein A applications in affinity chromatography there is a need in the art to provide novel Ig binding proteins with improved properties that specifically bind to immunoglobulins in order to facilitate affinity purification of immunoglobulins. To maximally exploit the value of the chromatographic matrices comprising Ig binding proteins it is desirable to use the affinity ligand matrices multiple times. Between chromatography cycles, a thorough cleaning procedure is required for sanitization and removal of residual contaminants on the matrix. In this procedure, it is general practice to apply alkaline solutions with high concentrations of NaOH to the affinity ligand matrices. Wild-type Protein A domains cannot withstand such harsh alkaline conditions for an extended time and quickly lose binding capacity for immunoglobulin. Accordingly, there is an ongoing need in this field to obtain novel alkaline-stable proteins capable of binding immunoglobulins.

The present invention provides alkaline stable immunoglobulin binding proteins that are particularly well-suited for affinity purification of immunoglobulins but overcome the disadvantages of the prior art. In particular, a significant advantage of the alkaline stable Ig binding proteins of the invention is their improved stability at high pH compared to a parental protein.

The above overview does not necessarily describe all problems solved by the present invention.

SUMMARY OF THE INVENTION

A first aspect of the present invention is to provide an Ig binding protein suitable for affinity purification. This is achieved with the alkaline stable Ig binding protein comprising one or more Ig binding domains, wherein at least one Ig binding domain comprises a variant of a parental amino acid sequence of SEQ ID NO: 1 or SEQ ID NO: 2 having at least 1, 2, 3, or 4 substitutions selected from the group consisting of an amino acid substitution to Isoleucine at position 1 or at a position corresponding thereto, an amino acid substitution to Alanine, Glutamic Acid, or Isoleucine at position 11 or at a position corresponding thereto, an amino acid substitution to Arginine or Isoleucine at position 35 or at a position corresponding thereto, and an amino acid substitution to Leucine at position 42 or at a position corresponding thereto. In some embodiments, the invention comprises of Ig binding protein wherein at least one Ig binding domain comprises a consensus amino acid sequence of SEQ ID NO: 52.

In a second aspect the present invention relates to an affinity separation matrix comprising the alkaline stable Ig binding protein of the first aspect.

In a third aspect the present invention relates to a use of the alkaline stable Ig binding protein of the first aspect or of the affinity separation matrix of the second aspect for affinity purification of immunoglobulins or proteins comprising an Fc part of immunoglobulins.

In a fourth aspect the present invention relates to a method of affinity purification of immunoglobulins or proteins comprising an Fc part of immunoglobulins comprising the steps of (a) providing a liquid containing an immunoglobulin; (b) providing an affinity separation matrix comprising an immobilized alkaline stable Ig binding protein of the first aspect coupled to said affinity separation matrix; (c) contacting said liquid and said affinity separation matrix, wherein said immunoglobulin binds to said immobilized Ig binding protein; and (d) eluting said immunoglobulin from said matrix, thereby obtaining an eluate containing said immunoglobulin. This summary of the invention does not necessarily describe all features of the present invention. Other embodiments will become apparent from a review of the ensuing detailed description.

BRIEF DESCRIPTION OF THE FIGURES

FIG. 1. Amino acid sequences of alkaline stable Ig binding domains. Positions 1, 11, 35, and 42 are shown in grey. The numbers in the top row refer to the corresponding amino acid position in the Ig binding domain.

FIG. 1A. Amino acid sequences of artificial alkaline stable Ig binding domains. Shown are embodiments cs14-1 (SEQ ID NO: 18), CS14-2 (SEQ ID NO: 19), CS14-4 (SEQ ID NO: 52), CS14-3 (SEQ ID NO: 20), CS25-1 (SEQ ID NO: 56), CS25-2 (SEQ ID NO: 26), CS74H1-1 (SEQ ID NO: 57), CS74H1-2 (SEQ ID NO: 42), CS74H2-1 (SEQ ID NO: 58), CS74H2-2 (SEQ ID NO: 43), CS74H3-1 (SEQ ID NO: 59), CS74H3-2 (SEQ ID NO: 44), CS74H4-1 (SEQ ID NO: 60), CS74H4-2 (SEQ ID NO: 45), CS27-1 (SEQ ID NO: 29), and CS27-2 (SEQ ID NO: 30).

FIG. 1B. Consensus amino acid sequence of alkaline stable artificial Ig binding domains (SEQ ID NO: 52).

Shown from top to bottom are embodiments as set forth in SEQ ID NO: 61, SEQ ID NO: 30, SEQ ID NO: 62, and SEQ ID NO: 63.

FIG. 2. Analysis of the alkaline stability of point mutation variants of parental IB14. The remaining activity (in %) of Ig binding after six hours of continuous 0.5 M NaOH treatment of variants with point mutations in positions 1, 11, 35, or 42 is compared to parental IB14.

FIG. 3. Analysis of the alkaline stability of different variants of parental IB14 with substitutions in positions 1, 11, and 35, and optionally in positions 28 and 42. The remaining activity (in %) of Ig binding after six hours of continuous 0.5 M NaOH treatment of combinations of substitutions in positions 1, 11, 28, 35, and/or 42 (black columns) is compared to the parental IB14 (light grey column). cs14-1 refers to SEQ ID NO: 18 (1I/11A/35R), cs14-2 refers to (1I/11A/35R/42L) SEQ ID NO: 19, cs14-3 refers to SEQ ID NO: 20 (1I/11A/28N/35R/42L).

FIG. 4. Analysis of the alkaline stability of different variants of parental IB27 with combinations of 3 or 4 substitutions in positions 1, 11, and 35, and optionally 42. The remaining activity (in %) of Ig binding after six hours of continuous 0.5 M NaOH treatment of variant Ig binding protein (black columns) is compared to the parental IB27 (light grey column). cs27-1 refers to SEQ ID NO: 29 (1I/11A/35R), cs27-2 refers to SEQ ID NO: 30 (1I/11A/35R/42L).

FIG. 5. Ig binding activity of Ig binding domains after alkaline treatment. Analysis of the alkaline stability of different Ig binding domains on epoxy resin after 6 h 0.5 M NaOH treatment. Shown are Ig binding domains with 1I, 11A, 35R, and 42L. Alkaline stable Ig binding domains: cs14-3 (SEQ ID NO: 20), cs74h1 (SEQ ID NO: 42), cs74h2 (SEQ ID NO: 43), cs47h3 (SEQ ID NO: 44), and cs47h4 (SEQ ID NO: 45), cs25-2 (SEQ ID NO: 26); parental domain: IB14.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are consistent with the definitions provided in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

The term "about", as used herein, encompasses the explicitly recited amounts as well as deviations therefrom of ±10%. More preferably, a deviation 5% is encompassed by the term "about".

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

In the context of the present invention, the term "immunoglobulin-binding protein" or "Ig binding protein" or "immunoglobulin (Ig) binding protein" is used to describe proteins that are capable to specifically bind to the Fc region of an immunoglobulin. Due to this specific binding to the Fc region, the "Ig binding proteins" of the invention are capable of binding to entire immunoglobulins, to immunoglobulin fragments comprising the Fc region, to fusion proteins comprising an Fc region of an immunoglobulin, and to conjugates comprising an Fc region of an immunoglobulin. While the Ig binding proteins of the invention herein exhibit specific binding to the Fc region of an immunoglobulin, it is not excluded that Ig binding proteins can additionally bind with reduced affinity to other regions, such as Fab regions of immunoglobulins.

In preferred embodiments of the present invention, the Ig binding protein comprises one or more alkaline stable Ig binding domains.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first protein and a second protein. In the context of the present invention, the term $K_D$ is particularly used to describe the binding affinity between an Ig binding protein and an immunoglobulin.

An Ig binding protein of the invention is considered to bind to an immunoglobulin, if it has a dissociation constant $K_D$ to immunoglobulin of at least 1 μM or less, or preferably 100 nM or less, more preferably 50 nM or less, even more preferably 10 nM or less.

The term "binding" according to the invention preferably relates to a specific binding. "Specific binding" means that an Ig binding protein of the invention binds stronger to an immunoglobulin for which it is specific compared to the binding to another non-immunoglobulin target.

The term "immunoglobulin" or "Ig" as used interchangeably herein, comprises proteins having a four-polypeptide chain structure consisting of two heavy chains and two light chains with the ability to specifically bind an antigen.

Furthermore, also fragments or variants thereof are comprised in the term "immunoglobulin". Ig fragments as understood herein comprise fewer amino acid residues than an intact or complete Ig. The term also includes embodiments such as chimeric (human constant domain, non-human variable domain), single chain and humanized (human antibody with the exception of non-human CDRs) immunoglobulins.

The "immunoglobulin" as understood herein can include, but is not necessarily limited to, mammalian IgG, such as human IgG$_1$, human IgG$_2$, human IgG$_4$, mouse IgG$_1$, mouse IgG$_2$A, mouse IgG$_2$ IgG$_1$, rat IgG$_2$C, goat IgG$_1$, goat IgG$_2$, bovine IgG$_2$, guinea pig IgG, rabbit IgG; human IgM, human IgA; and immunoglobulin fragments comprising a Fc region, fusion proteins comprising an Fc region of an immunoglobulin, and conjugates comprising an Fc region of an immunoglobulin. Notably, naturally occurring protein A domains and artificial Ig binding proteins of the invention do not bind to human IgG$_3$.

The terms "protein" and "polypeptide" refer to any linear molecular chain of two or more amino acids linked by peptide bonds and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Ig binding proteins comprising two or more protein domains also fall under the definition of the term "protein" or "polypeptides".

The term "alkaline stable" or "alkaline stability" or "caustic stable" or "caustic stability" (abbreviated as "cs" herein) refers to the ability of the Ig binding protein of the invention to withstand alkaline conditions without significantly losing the ability to bind to immunoglobulins. The skilled person in this field can easily test alkaline stability by incubating an Ig binding protein with sodium hydroxide solutions, e.g., as described in the Examples, and subsequent testing of the binding activity to immunoglobulin by routine experiments known to someone skilled in the art, for example, by chromatographic approaches.

Ig binding proteins of the invention as well as matrices comprising Ig binding proteins of the invention exhibit an "increased" or "improved" alkaline stability, meaning that the molecules and matrices incorporating said Ig binding proteins are stable under alkaline conditions for an extended period of time relative to a parental protein, i.e. do not lose the ability to bind to immunoglobulins or lose the ability to bind to immunoglobulins to a lesser extent than a parental protein.

The terms "binding activity" refer to the ability of an Ig binding protein of the invention to bind to immunoglobulin. For example, the binding activity can be determined before and/or after alkaline treatment. The binding activity can be determined for an Ig binding protein or for an Ig binding protein coupled to a matrix, i.e. for an immobilized binding protein. The term "artificial" refers to an object that is not naturally occurring, i.e. the term refers to an object that has been produced or modified by man. For example, a polypeptide or polynucleotide sequence that has been generated by man (e.g. for example in a laboratory by genetic engineering, by shuffling methods, or by chemical reactions, etc.) or intentionally modified is artificial.

The term "parental" in the term "parental protein" or "parental domain" as used herein refers to an Ig binding protein that is subsequently modified to generate a variant of said parental protein or domain. Said parental protein or domain may be an artificial domain (for example, but not limited to, SEQ ID NO: 3, 4, 10, 14, 21, 25, 47, 48, 49, 50), a naturally occurring Staphylococcus aureus Protein A domain, or a variant or engineered version of a naturally occurring Staphylococcus aureus Protein A domain.

The term "variant" or "variant Ig binding domain" or "Ig binding domain variant" or "Ig binding protein variant" as used herein includes an amino acid sequence of an Ig binding protein or domain that differs from that of a parental protein or domain amino acid sequence by at least one amino acid substitution compared to the parent. Furthermore, it refers to an artificial molecule that differs from a parent molecule by one or more modifications. These modifications may be generated by genetic engineering or by chemical synthesis or chemical reactions carried out by man. For example, domain Z is a variant of naturally occurring Protein A domain B. For example, SEQ ID NO: 30 is a variant of the parental protein IB27.

The term "conjugate" as used herein relates to a molecule comprising or essentially consisting of at least a first protein attached chemically to other substances such as to a second protein or a non-proteinaceous moiety.

The term "modification" or "amino acid modification" refers to an exchange, a deletion, or an insertion of an amino acid at a particular position in a parent polypeptide sequence by another amino acid. Given the known genetic code, and recombinant and synthetic DNA techniques, the skilled scientist can readily construct DNAs encoding the amino acid variants.

The term "substitution" or "amino acid substitution" refers to an exchange of an amino acid at a particular position in a parent polypeptide sequence by another amino acid. For example, the substitution S11A refers to a variant Ig binding protein, in which the serine at position 11 is replaced by an alanine. For the preceding example, 11A refers to an alanine at position 11. For the purposes herein, multiple substitutions are typically separated by a slash. For example, A1I/S11A/K35R refers to a variant comprising the combination of substitutions A1I, S11A, and K35R.

The term "deletion" or "amino acid deletion" refers to the removal of an amino acid at a particular position in a parent polypeptide sequence.

The term "insertions" or "amino acid insertion" refers to the addition of amino acids to the parent polypeptide sequence.

Throughout this description, the amino acid residue position numbering convention of FIG. 1 is used, and the position numbers are designated as corresponding to those for example in SEQ ID NOs: 1-8.

The term "amino acid sequence identity" refers to a quantitative comparison of the identity (or differences) of the amino acid sequences of two or more proteins. "Percent (%) amino acid sequence identity" or "percent identical" or "percent identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein. Methods for alignment are well-known in the art. For example, for determining the extent of an amino acid sequence identity of an arbitrary polypeptide relative to a reference amino acid sequence, the SIM Local similarity program is preferably employed (Xiaoquin Huang and Webb Miller (1991), Advances in Applied Mathematics, vol. 12: 337-357), that is freely available (see also: http://www.expasy.org/tools/sim-prot.html). For multiple alignment analysis ClustalW is preferably used (Thompson et al. (1994) Nucleic Acids Res., 22(22): 4673-4680). Preferably, the default parameters of the SIM Local similarity program or of ClustalW are used, when calculating sequence identity percentages.

In the context of the present invention, the extent of sequence identity between a modified sequence and the sequence from which it is derived is generally calculated with respect to the total length of the unmodified sequence, if not explicitly stated otherwise.

Each amino acid of the query sequence that differs from the reference amino acid sequence at a given position is counted as one difference. The sum of differences is then related to the length of the reference sequence to yield a percentage of non-identity. The quantitative percentage of identity is calculated as 100 minus the percentage of non-identity.

As used herein, the phrases "percent identical" or "percent (%) amino acid sequence identity" or "percent identity", in the context of two polypeptide sequences, refer to two or more sequences or subsequences that have in some embodiments at least 89.5%, in some embodiments at least 91%, in some embodiments at least 93%, in some embodiments at least 94%, in some embodiments at least 96%, in some embodiments at least 98%, and in some embodiments 100% nucleotide or amino acid residue identity, respectively, when compared and aligned for maximum correspondence, as measured using one of the following sequence comparison algorithms or by visual inspection. The percent identity exists in some embodiments over a region of at least about 50 residues, in some embodiments over a region of at least about 51 residues, in some embodiments over a region of at least about 52 residues, in some embodiments over a region of at least about 53 residues, in some embodiments over a region of at least about 54 residues, in some embodiments over a region of at least about 55 residues, in some embodiments over a region of at least about 56 residues, in some embodiments over a region of at least about 57 residues, and in some embodiments over a region of at least about 58 residues. In some embodiments, the percent identity exists over the entire length of the sequences.

The term "fused" means that the components are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide As used herein, the term "linker" refers in its broadest meaning to a molecule that covalently joins at least two other molecules. In typical embodiments of the present invention, a "linker" is to be understood as a moiety that connects an Ig binding domain with at least one further Ig binding domain, i.e. a moiety linking two protein domains to each other to generate a multimer. In preferred embodiments, the "linker" is a peptide linker, i.e. the moiety linking the two protein domains is one single amino acid or a peptide comprising two or more amino acids.

The term "chromatography" refers to separation technologies which employ a mobile phase and a stationary phase to separate one type of molecules (e.g., immunoglobulins) from other molecules (e.g. contaminants) in the sample. The liquid mobile phase contains a mixture of molecules and transports these across or through a stationary phase (such as a solid matrix).

Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific binding affinity for the molecule to be purified. As understood in the context of the invention, affinity chromatography involves the addition of a sample containing an immunoglobulin to a stationary phase which comprises a chromatography ligand, such as an Ig binding protein of the invention.

The terms "solid support" or "solid matrix" are used interchangeably for the stationary phase. The terms "affinity matrix" or "affinity separation matrix" or "affinity chromatography matrix", as used interchangeably herein, refer to a matrix, e.g. a chromatographic matrix, onto which an affinity ligand e.g., an Ig binding protein of the invention is attached. The ligand (e.g., Ig binding protein) is capable of specific binding to a molecule of interest (e.g., an immunoglobulin as defined above) which is to be purified or removed from a mixture.

The term "affinity purification" as used herein refers to a method of purifying immunoglobulins as defined above from a liquid by binding the immunoglobulins as defined above to an Ig binding protein that is immobilized to a matrix. Thereby, all other components of the mixture except immunoglobulins are removed. In a further step, the bound immunoglobulins can be eluted in purified form.

EMBODIMENTS OF THE INVENTION

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to an Immunoglobulin (Ig) binding protein, comprising one or more Ig binding domains, wherein at least one Ig binding domain comprises, essentially consists of, or consists a variant of a parental amino acid sequence having at least 1, 2, 3 or 4 substitutions selected from the group consisting of an amino acid substitution to Isoleucine at position 1, an amino acid substitution to Alanine, Glutamic Acid, or Isoleucine at position 11, an amino acid substitution to Arginine or Isoleucine at position 35, and an amino acid substitution to Leucine at position 42. In some embodiments, the said at least one variant Ig binding domain further comprises 1, 2, 3, 4, 5, or 6 modifications, wherein each individual modification is selected from the group consisting of a single amino acid substitutions, a single amino acid deletion, a single amino acid insertions.

The advantage of the variant Ig binding protein is that they are stable under alkaline conditions for an extended period of time. This feature is important for chromatography approaches with cleaning procedures using alkaline solutions with high NaOH concentrations to remove contaminants on the matrix so for example that the matrix can be used several time. The variant Ig binding proteins are more stable after alkaline treatment compared to parental polypeptides. Said substitutions at positions 1, 11, 35, and/or 42 in the parental proteins as defined above confer an improved alkali stability in comparison with the parental protein, without impairing the immunoglobulin-binding properties.

Parental SEQ ID NO: 1.

In some embodiments, the Immunoglobulin binding protein is comprising one or more Ig binding domains of a variant of (i) an amino acid sequence of SEQ ID NO: 1 or of a variant of (ii) an amino acid sequence exhibiting at least 89.5% sequence identity to the amino acid sequence of SEQ ID NO: 1. Said Ig binding domain has at least 1, 2, 3, or 4 substitutions selected from the group consisting of an amino acid substitution to Isoleucine at position 1 of SEQ ID NO: 1, an amino acid substitution to Alanine, Glutamic Acid, or Isoleucine at position 11 of SEQ ID NO: 1, an amino acid substitution to Arginine or Isoleucine at position 35 of SEQ ID NO: 1, and an amino acid substitution to Leucine at position 42 of SEQ ID NO: 1. Said variant Ig binding protein might comprise additional modifications, such as 1, 2, 3, 4, 5, or 6 substitutions or 1, 2, 3, 4, 5, 6 deletions.

The Ig binding domains shown in SEQ ID NO: 1 are parental domains; the Ig binding domains with substitutions at least in positions 1, 11, 35, and/or 42 are variants of SEQ ID NO: 1.

SEQ ID NO: 1 is a consensus sequence covering parental domains for variants of the invention, preferably (i) artificial Ig binding domains including SEQ ID NOs: 3, 4, 10, 14, 21, 25, 47, 48, 49, 50; (ii) naturally occurring Protein A domains or variants including SEQ ID NOs: 5-8. The parental protein of SEQ ID NO: 1 is the following amino acid sequence: $X_1X_2X_3X_4X_5X_6X_7X_8QQX_{11}AFYX_{15}X_{16}LX_{18}X_{19}PX_{21}LX_{23}X_{24}X_{25}QRX_{28}X_{29}FIQSLKDDPSX_{40}SX_{42}X_{43}X_{44}LX_{46}EAX_{49}KLX_{52}X_{53}X_{54}X_{55}APX_{58}$ wherein the amino acid at position 1 ($X_1$) is selected from P, N, A, V, or Q, the amino acid at position 2 ($X_2$) is selected from A, D, or Q, the amino acid at position 3 ($X_3$) is selected from A, N, or S, preferably A or N, the amino acid at position 4 ($X_4$) $X_4$ is selected from K or N, preferably K, the amino acid at position 5 ($X_5$) is selected from H or F, the amino acid at position 6 ($X_6$) is selected from D, N, A, or S, preferably D or N, the amino acid at position 7 ($X_7$) is selected from K or E, the amino acid at position 1 ($X_8$) is selected from D, A, or E, the amino acid at position 11 ($X_{11}$) is selected from S or N, the amino acid at position 1 ($X_{15}$) is selected from E or Q, the amino acid at position 16 ($X_{16}$) is selected from I or V, the amino acid at position 18 ($X_{18}$) is selected from H or N, the amino acid at position 19 ($X_{19}$) $X_{19}$ is selected from L or M, the amino acid at position 21 ($X_{21}$) is selected from N, S, or D, preferably N, the amino acid at position 23 ($X_{23}$) is selected from T or N, the amino acid at position 24 ($X_{24}$) is selected from E or A, the amino acid at position 25 ($X_{25}$) is selected from D or E, the amino acid at position 28 ($X_{28}$) is selected from S, N, or A, preferably N or S, the amino acid at position 29 ($X_{29}$) is selected from A or G, the amino acid at position 40 ($X_{40}$) is selected from V, Q, or T, preferably V or Q, the amino acid at position 42 ($X_{42}$) is selected from K, A, or T, the amino acid at position 43 ($X_{43}$) is selected from E, N or S, preferably E or N, the amino acid at position 44 ($X_{44}$) is selected from I, V, or L, the amino acid at position 46 ($X_{46}$) is selected from G or A, the amino acid at position 49 ($X_{49}$) is selected from K or Q, the amino acid at position 52 ($X_{52}$) is selected from N, D, or S, preferably N, the amino acid at position 53 ($X_{53}$) is selected from D or E, the amino acid at position 54 ($X_{54}$) is selected from A or S, and the amino acid at position 58 ($X_{58}$) is selected from P or K.

Parental SEQ ID NOs: 5-8.

In an embodiment of the first aspect, the parental domain comprises or essentially consists or consists of an amino acid sequence of SEQ ID NOs: 5-8, or an amino acid sequence exhibiting at least 89.5% sequence identity to an amino acid sequence of SEQ ID NOs: 5-8. The Ig binding domain comprises of a variant having at least 1, 2, 3, or 4 amino acid substitutions selected from the group consisting of an amino acid substitution to Isoleucine at position 1, an amino acid substitution to Alanine, Glutamic Acid, or Isoleucine at position 11, an amino acid substitution at position 35 to Arginine or Isoleucine, and an amino acid substitution to Leucine at position 42. In some embodiments, the Ig binding domain further comprises 1, 2, 3, 4, 5, or 6 modifications, wherein each individual modification is selected from the group consisting of a single amino acid substitutions, a single amino acid deletion, a single amino acid insertions.

Parental SEQ ID NO: 2.

In another preferred embodiment of the first aspect, wherein said at least one Ig binding domain comprises a variant of an parental amino acid sequence of SEQ ID NO: 2 wherein the variant has at least 1, 2, 3 or 4 substitutions selected from the group consisting of an amino acid substitution to Isoleucine at position 1 of SEQ ID NO: 2, an amino acid substitution to Alanine, Glutamic Acid, or Isoleucine at position 11 of SEQ ID NO: 2, an amino acid substitution at position 35 to Arginine or Isoleucine of SEQ ID NO: 2, and an amino acid substitution to Leucine at position 42 of SEQ ID NO: 2. In some embodiments, said at least one Ig binding domain further comprises 1, 2, 3, 4, 5, or 6 modifications, wherein each individual modification is selected from the group consisting of a single amino acid substitutions, a single amino acid deletion, a single amino acid insertions.

SEQ ID NO: 2 is a consensus sequence for preferred parental proteins such as but not limited to artificial Ig binding domains IB14, IB25, IB27, IB74, and IB47. Preferably, the invention relates to an Ig binding protein, wherein said at least one Ig binding domain comprises, essentially consists of, or consists of a variant of an amino acid sequence of parental SEQ ID NO: 2, or of a variant of an amino acid sequence with at least 89.5% identity to parental SEQ ID NO: 2. SEQ ID NO: 2 is a preferred embodiment of SEQ ID NO: 1: $X_1AAX_4X_5DX_7X_8QQX_{11}AFYEILHLPNLTEX_{25}QRX_{28}AFIQSLKDDPSVSKEX_{44}LX_{46}EAX_{49}KLNDX_{54}QAPX_{58}$ wherein the amino acid at position 1 ($X_1$) is selected from P, N, or A, the amino acid at position 5 ($X_5$) is selected from H or F, the amino acid at position 7 ($X_7$) is selected from K or E, the amino acid at position 8 ($X_8$) is selected from D, A, or E, the amino acid at position 11 ($X_{11}$) is selected from S or N, preferably S, the amino acid at position 25 ($X_{25}$) is selected from D or E, the amino acid at position 28 ($X_{28}$) is selected from S or N, preferably N, the amino acid at position 44 ($X_{44}$) is selected from I or V, the amino acid at position 46 ($X_{46}$) is selected from G or A, the amino acid at position 49 ($X_{49}$) is selected from K or Q, the amino acid at position 54 ($X_{54}$) is selected from A or S, and the amino acid at position 58 ($X_{58}$) is selected from P or K.

Exemplary Parental Proteins.

In some embodiments, said Ig binding domain comprises a variant of parental amino acid sequences selected from the group consisting of SEQ ID NO: 3, 4, 10, 14, 21, 25, 47-50, wherein the variant has at least 1, 2, 3, or 4 amino acid substitutions selected from the group consisting of an amino acid substitution of Alanine or Proline to Isoleucine at position 1, an amino acid substitution of Serine to Alanine, Glutamic Acid, or Isoleucine at position 11, an amino acid substitution of Lysine at position 35 to Arginine or Isoleucine, and an amino acid substitution of Lysine to Leucine at position 42.

IB14 as Parental Protein.

In a preferred embodiment of the first aspect, the parental protein is the amino acid sequence of SEQ ID NO: 3, or a protein having at least 89.5% identity to parental SEQ ID NO: 3. Examples for parental proteins with at least 89.5% identity to SEQ ID NO: 3 may be selected from the group consisting of SEQ ID NO: 21 (1P/28N), SEQ ID NO: 10 (1A/28S), SEQ ID NO: 14 (1P/28S), SEQ ID NO: 25 (46A/58K), SEQ ID NO: 47 (5F/7E/8A), SEQ ID NO: 48 (5F/7E/8A/25E), SEQ ID NO: 49 (44V/49Q/54S/58K), SEQ ID NO: 50 (25E/44V/49Q/54S/58K), IB13 (1P/4Q/28S), IB23 (1P/21S/28A/40T/43S), IB15 (2D/3N/5F/7E/8A/28A), and IB16 (2D/3S/5F/7E/8A/28A).

IB27 as Parental Protein.

In another preferred embodiment of the first aspect, the parental protein is SEQ ID NO: 4, or a protein having at least 89.5% identity to parental SEQ ID NO: 4. Examples for parental proteins with at least 89.5% identity are selected from the group consisting of SEQ ID NO: 50 (5H/7K/8D), SEQ ID NO: 49 (5H/7K/8D/25D), SEQ ID NO: 48 (44I/49K/54A/58P), and SEQ ID NO: 47 (25D/44I/49K/54A/58P).

Further Preferred Parental Domains.

In an embodiment of the first aspect, the parental protein is the amino acid sequence of SEQ ID NO: 25. In another embodiment of the first aspect, the parental protein is the amino acid sequence of SEQ ID NO: 50 or SEQ ID NO: 49. In another embodiment of the first aspect, the parental protein is the amino acid sequence of SEQ ID NO: 48 or SEQ ID NO: 47.

Preferred Amino Acid Positions in Alkaline Stable Proteins.

In some embodiment, said Ig binding domain of the variant Ig binding protein comprises a substitution or a plurality of substitutions.

The substitution in position 1 to Isoleucine (I) may be the only substitution (for example, SEQ ID NO: 9) or the Ig binding domain may comprise further mutations, such as at least substitutions in positions 11 and/or 35 and/or 42 in parental proteins. It is preferred that the amino acid in position 1 of the alkaline stable protein is not Threonine (T). It is preferred that the amino acid in position 1 is Isoleucine (I) or Alanine (A).

The substitution in position 11 to Alanine (A), Glutamic Acid (E), or Isoleucine (I) may be the only substitution (for example, SEQ ID NOs: 11-13) or the Ig binding domain may comprise further mutations, preferably at least substitutions in positions 1 and/or 35 and/or 42. It is preferred that the amino acid in position 11 is not Asparagine (N) or Lysine (K). It is preferred that the amino acid in position 11 is Alanine (A), Isoleucine (I), Glutamic acid (E), Histidine (H) or Proline (P), more preferred A, I, or E, most preferred A.

The substitution in position 35 to Arginine (R) or Isoleucine (I) may be the only substitution (for example, SEQ ID NOs: 15-16) or the Ig binding domain may comprise further mutations, preferably at least substitutions in positions 1 and/or 11 and/or 42. It is preferred that the amino acid in position 35 is not Proline (P), Asparagine (N), Glycine (G), Tryptophan (W), Alanine (A), Glutamine (Q), or Methionine (M). It is preferred that the amino acid in position 35 is R or I. The substitution in position 42 to Leucine (L) may be the only substitution (for example, SEQ ID NO: 17) or the Ig binding domain may comprise further mutations, preferably at least substitutions in positions 1 and/or 11 and/or 35. It is preferred that the amino acid in position 42 is not Tyrosine (Y). It is preferred that the amino acid in position 42 is L.

Preferred Combinations of Amino Acids in Ig Binding Domains.

Surprisingly, a specific combination of amino acids in positions 1, 11, and 35, and optionally in positions 1, 11, 35, 42 and optionally in positions 1, 11, 28, 35, and 42 increase the alkaline stability of the variant Ig binding domain compared to a parental domain, as shown in the Figures and in the Examples. In addition to substitutions in positions 1, 11, 35, 42, alkaline stable Ig binding domains might comprise additional 1, 2, or 3 modifications, such as substitutions, deletions, or insertions. For example, the at least one Ig binding domain comprise a substitution or substitutions compared to parental sequences and wherein the substitution or a plurality of substitutions are at least selected from the group consisting of: 1I; 11A; 35R; 42L; 11E; 11I; 35I; 1I/11A; 1I/35R; 11A/35R; 1I/42L; 11A/42L; 1I/11E; 1I/11I; 11I/35R; 11E/35R; 11I/42L; 11E/42L; 1I/35I; 11A/35I; 1I/35I; 11E/35I; 35R/42L; 35I/42L; 1I/11A/35R; 1I/11E/35R; 1I/11I/35R; 1I/11A/42L; 1I/11E/42L; 1I/11I/42L; 1I/11A/35I; 1I/11E/35I; 1I/11I/35I; 1I/35R/42L; 1I/35I/42L; 11I/35R/42L; 11I/35I/42L; 11A/35R/42L; 11A/35I/42L; 11E/35R/42L; 11E/35I/42L; 1I/11A/35R/42L; 1I/11E/35R/42L; 1I/11I/35R/42L; 1I/11A/35I/42L; 1I/11E/35I/42L; 1I/11I/35I/42L; 1I/11A/28N/35R/42L; 1I/11E/28N/35R/42L; 1I/11I/28N/35R/42L; 1I/11A/28N/35I,42L; 1I/11I/28N/35I/42L; and 1I/11E/28N/35I/42L. Preferred are substitutions selected from the group consisting of 1I; 11A; 35R; 42L; 1I/11A; 1I/35R; 1I/42L; 11A/42L; 11A/35R; 35R/42L; 1I/11A/35R; 1I/11A/42L; 1I/11A/35R/42L; and 1I/11A/28N/35R/42L. In some embodiments, 3 or 4 of the amino acid positions are selected from the group consisting of 1I, 11A, 35R, and 42L. In other embodiments, Ig binding domains comprise the combination of substitutions selected from the group consisting of 1I/11A/35R; 1I/11A/35R/42L; and 1I/11A/28N/35R/42L.

In preferred embodiments, the Ig binding protein of the invention comprises or essentially consists of one or more Ig binding domains, wherein the amino acid residue at position 1 is Isoleucine, and wherein the amino acid residue at position 11 is Alanine. Another preferred Ig binding protein of the invention comprises or essentially consists of one or more Ig binding domains, wherein the amino acid residue at position 1 is Isoleucine, and wherein the amino acid residue at position 11 is Alanine, and wherein the amino acid residue at the position 35 is Arginine. Another preferred Ig binding protein of the invention comprises or essentially consists of one or more Ig binding domains, wherein the amino acid residue at position 1 is Isoleucine, and wherein the amino acid residue at position 11 is Alanine, and wherein the amino acid residue at the position 35 is Arginine, and wherein the amino acid residue at position 42 is Leucine. Another preferred Ig binding protein of the invention comprises or essentially consists of one or more Ig binding domains, wherein the amino acid residue at position 1 is Isoleucine, and wherein the amino acid residue at position 11 is Alanine, and wherein the amino acid residue at the position 35 is Arginine, and wherein the amino acid residue at position 42 is Leucine, and wherein the amino acid residue at position 28 is Asparagine. Another preferred Ig binding protein of the invention comprises or essentially consists of one or more Ig binding domains, wherein the amino acid residue at position 11 is Alanine, and wherein the amino acid residue at the position 35 is Arginine, and wherein the amino acid residue at position 42 is Leucine.

Sequences of Alkaline Stable Proteins.

An Ig binding protein of the invention is comprising one or more Ig binding domains that comprises or essentially consists or consists of the amino acid sequence of SEQ ID NO: 52. In some embodiments, an Ig binding domain comprises of at least 89.5% identical amino acid sequences to SEQ ID NO: 52. SEQ ID NO: 52 is a consensus sequence for preferred artificial Ig binding proteins such as Ig binding domains of, for example, SEQ ID NO: 18-20, 26, 29-30, 42-45, 56-61. SEQ ID NO: 52 is the following amino acid sequence (see FIG. 1B): IAAKX$_5$DX$_7$X$_8$QQAAFYEILHLPNLTEX$_{25}$QRX$_{28}$AFIQS LRDDPSVSX$_{42}$EX$_{44}$LX$_{46}$EAX$_{49}$KLNDX$_{54}$QA PX$_{58}$ wherein the amino acid at position 5 (X$_5$) is selected from H or F, the amino acid at position 7 (X$_7$) is selected from K or E, the amino acid at position 8 (X$_8$) is selected from D, A, or E, the amino acid at position 25 (X$_{25}$) is selected from D or E, the amino acid at position 28 (X$_{28}$) is selected from S or N, the amino acid at position 42 (X$_{42}$) is selected from L or K, preferably L, the amino acid at position 44 (X$_{44}$) is selected from I or V, the amino acid at position 46 (X$_{46}$) is selected from G or A, the amino acid at position 49 (X$_{49}$) is selected from K or Q, the amino acid at position 54 (X$_{54}$) is selected from A or S, and the amino acid at position 58 (X$_{58}$) is selected from P or K.

High Alkaline Stability as Result of the Combination of 3 or 4 Amino Acids in Positions 1, 11, 35, 42 in Ig Binding Proteins.

In some embodiments, the combination of at least 3 or 4 amino acids selected from Isoleucine in position 1 Alanine in position 11, Arginine in position 35, and Leucine in position 42 provide surprisingly particularly good alkaline stability of the Ig binding protein, as shown in the Examples and in the Figures. It is preferred that position 28 is Asparagine. As shown in the examples below, all Ig binding proteins of the invention were found to bind to Ig even after alkaline treatment. The Ig binding protein of the invention exhibits an high alkaline stability for at least 6 h in 0.5 M NaOH, in particular an improved alkaline stability as compared to a corresponding parental protein.

It was surprising and unexpected that the Ig binding proteins with the combination of at least 3 or 4 amino acids at amino acid position 1 to Isoleucine, at amino acid position 11 to Alanine, Glutamic Acid, or Isoleucine, at amino acid position 35 to Arginine or Isoleucine, and optionally at amino acid position 42 to Leucine are able to bind to Ig even after alkaline treatment for several hours. It was most surprising and unexpected that the Ig binding proteins comprising a combination of amino acids 1I, 11A or 11E or 11I, 35R or 35I, and optionally 42L, preferably 1I, 11A, 35R, and 42L are able to bind to Ig even after alkaline treatment for several hours. The alkaline stability of the Ig binding protein is determined by comparing the loss in Ig binding activity after 6 h incubation in 0.5 M NaOH. In some embodiments, this is compared to the loss in Ig-binding activity of the corresponding parental protein. The loss of binding activity is determined by comparing binding activity before and after 0.5 M NaOH incubation for 6 hours.

As shown by the comparative data in the Figures, the Ig binding activity of the Ig binding domains with at least 3 or 4 amino acids selected from 1I, 11A or 11E or 11I, 35R or 35I, and 42L is increased by at least 25% compared to a parental protein. This is a surprising and advantageous property as compared to parental proteins.

Preferred alkaline stable Ig binding proteins. In specific embodiments, the Ig binding domain comprises of an amino acid sequence selected from the group consisting of SEQ ID NOs: 18-20, 26, 29-40, 42-45, and 56-61. In some embodiments, the domain comprises amino acid sequences of the group consisting of SEQ ID NOs: 20, 26, 30, 42-45. The alkaline stable domains might comprise further modifications, such as insertions, deletions, or further substitutions. In some embodiments, Ig binding domains have 1, 2, 3, 4, 5, or 6 further substitutions. In other embodiments, Ig binding domains have a deletion of 1, 2, 3, or 4 amino acids within the first 4 amino acids of its N-terminus and/or a deletion of 1 or 2 amino acids at the C-terminus. In some embodiments, Ig binding domains have deletions at the N-terminus, for example in positions 1, 2, and 4, or in positions 1, 2, and 3. In some embodiments, Ig binding domains have deletions at the C-terminus, for example in positions 57 and/or 58. Some embodiments relate to sequences with at least 89.5% sequence identity to an amino acid selected from the group consisting of SEQ ID NOs: 20, 26, 30, 42-45, for example but not limited to SEQ ID NOs: 9-19, 29, 53-54, 56-61. Some embodiments relate to amino acid sequences with at least 89.5% sequence identity to the amino acid sequence to any of the afore-mentioned SEQ ID NOs, wherein the amino acid sequence with at least 89.5% sequence identity to any of the afore-mentioned SEQ ID NOs has the same amino acids in at least 3 or 4 of positions 1, 11, 35 and 42 or positions corresponding to the respective amino acid positions in the sequences SEQ ID NOs: 20, 26, 29, 30, 42-45, from which said amino acid sequence with at least 89.5% sequence identity was derived. The sequences for preferred alkaline stable Ig binding proteins are shown in FIG. 1. It is preferred that at least 3 or 4 of positions 1I, 11A, 35R, and 42L are conserved. It is further preferred that position 4 is not Q.

SEQ ID NO: 20 (Cs14) and Variants.

In a specific embodiment, the alkaline stable Ig binding domain comprises, or essentially consists, or consists of an amino acid sequence of SEQ ID NO: 20 or an amino acid sequence at least 91% identical thereto, for example SEQ ID NOs: 18-19, 26, 42-45, 56. In preferred embodiments, variants of SEQ ID NO: 20 do not have a Q in position 4. It is further preferred that position 4 is K. In a specific embodiment, the Ig binding domain comprises an amino acid sequence of SEQ ID NO: 20 or an amino acid sequence at least 96% identical thereto. For example, FIG. 3 and FIG. 5 show the remaining activity of Ig binding after prolonged continuous 0.5 M NaOH treatment.

Table 1 illustrates the amino acid differences of SEQ ID NO: 20 and preferred variants at least 91% identical thereto. It is preferred that position 5 is H or F, position 7 is K or E, position 8 is D or A, position 25 is D or E, position 44 is I or V, position 46 is G or A, position 49 is K or Q, position 54 is A or S, and position 58 is P or K. It is further preferred that position 4 is K. The identity of the artificial alkaline stable SEQ ID NO: 20 to any wildtype Protein A domain is below 78%.

TABLE 1

Amino acid differences of cs14 and variants with at least 91% sequence identity

| SEQ NO: | Ig binding protein | Pos. 5 | Pos. 7 | Pos. 8 | Pos. 25 | Pos. 44 | Pos. 46 | Pos. 49 | Pos. 54 | Pos. 58 | differences | identity (%) |
|---|---|---|---|---|---|---|---|---|---|---|---|---|
| 20 | cs14 | H | K | D | D | I | G | K | A | P | 0 | 100 |
| 26 | cs25 | H | K | D | D | I | A | K | A | K | 2 | 96.5 |
| 42 | cs74h1 | F | E | A | D | I | G | K | A | P | 3 | 94.8 |
| 43 | cs74h2 | F | E | A | E | I | G | K | A | P | 4 | 93.1 |
| 44 | cs47h3 | H | K | D | D | V | G | Q | S | K | 4 | 93.1 |
| 45 | cs47h4 | H | K | D | E | V | G | Q | S | K | 5 | 91.3 |

SEQ ID NO: 30 (Cs27) and Variants.

In a specific embodiment, the Ig binding domain comprises or essentially consists or consists of an amino acid sequence of SEQ ID NO: 30, or an amino acid sequence at least 94% identical thereto, for example SEQ ID NO: 29. The identity of SEQ ID NO: 30 to any wildtype Protein A domain is below 76%. FIG. 4 shows the remaining activity SEQ ID NOs: 30 and 29 after six hours of continuous 0.5 M NaOH treatment.

SEQ ID NO: 26 (Cs25) and Variants.

In a specific embodiment, the Ig binding domain comprises or essentially consists or consists of an amino acid sequence of SEQ ID NO: 26 or an amino acid sequence at least 98% identical thereto. The identity of SEQ ID NO: 26 to any wildtype Protein A domain is below 81%. FIG. 5 shows the remaining Ig binding activity of SEQ ID NO: 26 after six hours of continuous 0.5 M NaOH treatment.

SEQ ID NO: 42 (cs74) and Variants.

In an specific embodiment, the alkaline stable Ig binding domain comprises or essentially consists or consists of an amino acid sequence of SEQ ID NO: 42 and an amino acid sequence at least 98% identical thereto, for example SEQ ID NO: 43. The identity of SEQ ID NO: 42 to any wildtype Protein A domain is below 78%. FIG. 5 shows the remaining Ig binding of SEQ ID NOs: 42-43 after six hours of continuous 0.5 M NaOH treatment.

SEQ ID NO: 44 (Cs47) and Variants Thereof.

In an specific embodiment, the alkaline stable Ig binding domain comprises or essentially consists or consists of an amino acid sequence of SEQ ID NO: 44 and an amino acid sequence at least 98% identical thereto, for example SEQ ID NO: 45. The identity of SEQ ID NO: 44 to any wildtype Protein A domain is below 78%. FIG. 5 shows the remaining activity of Ig binding after six hours of continuous 0.5 M NaOH treatment of SEQ ID NOs: 44-45 with at least 98% identity.

Affinity to Immunoglobulin.

All Ig binding proteins of the invention bind to Immunoglobulin with a dissociation constant $K_D$ preferably below 1 µM, or below 100 nM, even more preferably 10 nM or less. Methods for determining binding affinities of Ig binding proteins or domains, i.e. for determining the dissociation constant $K_D$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Some of the methods are described further in the Examples. Typically, the dissociation constant $K_D$ is determined at 20° C., 25° C., or 30° C. If not specifically indicated otherwise, the $K_D$ values recited herein are determined at 22° C.+/−3° C. by surface plasmon resonance. In an embodiment of the first aspect, the Ig binding protein has a dissociation constant $K_D$ to human $IgG_1$ in the range between 0.1 nM and 100 nM, preferably between 0.1 nM and 10 nM.

Multimers.

In one embodiment of the invention, the Ig binding protein comprises 1, 2, 3, 4, 5, 6, 7, or 8, preferably 2, 3, 4, 5, or 6, Ig binding domains linked to each other, i.e. the Ig binding protein can be, for example, a monomer, a dimer, a trimer, a tetramer, a pentamer, or a hexamer. A multimer may comprise two, three, four, or even more binding domains.

Multimers of the invention are fusion proteins generated artificially, generally by recombinant DNA technology well-known to a skilled person. Ig binding proteins of the invention may be prepared by any of the many conventional and well-known techniques such as plain organic synthetic strategies, solid phase-assisted synthesis techniques or by commercially available automated synthesizers.

In some preferred embodiments, the multimer is a homo-multimer, e.g. the amino acid sequences of all alkaline stable Ig binding domains of the Ig binding protein are identical. An alkali-stable multimer may comprise two or more Ig binding domains, wherein said Ig binding domains preferably comprise or essentially consist of a sequence selected from the group consisting of SEQ ID NOs: 18-20, 26, 29-38, 42-45, 56-61 or a sequence with at least 89.5% sequence identity to any of the afore-mentioned SEQ ID NOs. In some embodiments, the domains are derivatives of SEQ ID NOs: 18-20, 26, 29-38, 42-45, 56-61 and further wherein each derivative has a deletion of 1, 2, or 3 amino acids within the first 4 amino acids of its N-terminus and/or a deletion of 1 or 2 amino acids at the C-terminus relative to the one of SEQ ID NOs: 18-20, 26, 29-38, 42-45, 56-61 upon which it is based (see, for example, SEQ ID NOs: 23, 24, 27).

For example, SEQ ID NO: 14 and SEQ ID NO: 20 were used to generate the homo-multimeric fusion constructs (dimers, tetramers, pentamers, and hexamers) described herein in Example 1.

In addition, dimers, tetramers, pentamers, and hexamers of SEQ ID NO: 30 were generated.

See for example SEQ ID NO: 23, 24, 27, 28.

In some embodiments of the first aspect, the multimer is a hetero-multimer, e.g. at least one alkaline stable Ig binding domain has a different amino acid sequence than the other Ig binding domains within the immunoglobulin-binding protein.

Linker.

In some embodiments of the first aspect, the one or more Ig binding domains are directly linked to each other. In other embodiments, the one or more Ig binding domains are linked to each other with one or more linkers. Preferred in these typical embodiments are peptide linkers. This means that the peptide linker is an amino acid sequence that connects a first Ig binding domain with a second Ig binding domain. The peptide linker is connected to the first Ig binding domain and to the second Ig binding domain by a peptide bond between the C-terminal and N-terminal ends of the domains, thereby generating a single, linear polypeptide chain. The length and composition of a linker may vary between at least one and up to about 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acids. It is preferred that the amino acid sequence of the peptide linker is stable against caustic conditions and proteases. Linkers should not destabilize the conformation of the domains in the Ig binding protein. Well-known are linkers comprising small amino acids such as glycine and serine. The linkers can be glycine-rich (e.g., more than 50% of the residues in the linker can be glycine residues). Also preferred are linkers that comprise further amino acids. Other embodiments of the invention comprise linkers consisting of alanine, proline, and serine. Other linkers for the fusion of proteins are known in the art and can be used.

Conjugation to a Solid Support.

In some embodiments of the invention, the Ig binding protein is conjugated to a solid support. In some embodiment of the invention, the Ig binding domain comprises an attachment site for site-specific covalent coupling of the Ig binding protein to a solid support. In some embodiments of the invention, the Ig binding protein may also comprise additional amino acid residues at the N- and/or C-terminal end, such as for example a leader sequence at the N-terminal end and/or a coupling sequence with or without a tag at the N- or C-terminal end (see for example SEQ ID NOs: 39 and 40). In some embodiments, the alkaline stable Ig binding protein comprises an attachment site for covalent attachment to a solid phase (matrix). Preferably, the attachment site is specific to provide a site-specific attachment to the solid phase. Specific attachment sites comprise natural amino acids, such as cysteine or lysine, which enable specific chemical reactions with a reactive group of the solid phase or a linker between the solid phase and the protein, for example selected from N-hydroxysuccinimide, iodoacetamide, maleimide, epoxy, or alkene groups. The attachment site may be directly at the C- or N-terminal end of the Ig binding protein or there may be a linker between the N- or C-terminus and the coupling site, preferably a peptide linker. In some embodiments of the invention, the Ig binding protein may comprise a short N- or C-terminal peptide sequence of 3-20 amino acids, preferably 4-10 amino acids, with a terminal cysteine. Amino acids for a C-terminal attachment site may be preferably selected from proline, alanine, and serine, for example, ASPAPSAPSAC (SEQ ID NO: 41), with a single cysteine at the C-terminal end for coupling. In another embodiment, amino acids for a C-terminal attachment site may be preferably selected from glycine and serine, for example, GGGSC, with a single cysteine at the C-terminal end for coupling.

An advantage of having a C-terminal cysteine is that coupling of the Ig binding protein can be achieved through reaction of the cysteine thiol with an electrophilic group on a support resulting in a thioether bridge coupling. This provides excellent mobility of the coupled protein which provides increased binding capacity.

In alternative embodiments, the coupling of the Ig binding protein to a solid support can be achieved through a cysteine in positions 43, 46, or 47 of an alkaline stable Ig binding domain. If a cysteine is located in positions 43, 46, or 47, the amino acid in position 50 or position 58 is not cysteine (see for example SEQ ID NOs: 53 or 54). Preferably the amino acid in position 50 is Lysine and the amino acid in position 58 is selected from Proline or Lysine.

Affinity Separation Matrix.

In another aspect the present invention is directed to an affinity separation matrix, comprising an Ig binding protein of the first aspect.

In preferred embodiments of the second aspect, the affinity separation matrix is a solid support. The affinity separation matrix comprises at least one Ig binding protein of the invention. This matrix comprising the alkaline stable Ig binding protein of the invention is useful for separation, for example for chromatographic separation, of immunoglobulins as defined above, i.e. Ig, Ig variants comprising the Fc region, fusion proteins comprising an Fc region of an Ig, and conjugates comprising an Fc region of an Ig. An affinity matrix is useful for separation of immunoglobulins and should retain the Ig binding property even after highly alkaline conditions as applied during cleaning processes. Such cleaning of matrices is essential for long-term repeated use of matrices.

Solid support matrices for affinity chromatography are known in the art and include for example but are not limited to, agarose and stabilized derivatives of agarose (e.g. Sepharose 6B, Praesto™Pure; CaptivA®, rPROTEIN A Sepharose Fast Flow, Mabselect®, and other), cellulose or derivatives of cellulose, controlled pore glass (e.g. ProSep® vA resin), monolith (e.g. CIM® monoliths), silica, zirconium oxide (e.g. CM Zirconia or CPG®), titanium oxide, or synthetic polymers (e.g. polystyrene such as Poros 50A or Poros MabCapture® A resin, polyvinylether, polyvinyl alcohol, polyhydroxyalkyl acrylates, polyhydroxyalkyl methacrylates, polyacrylamides, polymethacrylamides etc) and hydrogels of various compositions. In certain embodiments the support comprises a polyhydroxy polymer, such as a polysaccharide. Examples of polysaccharides suitable for supports include but are not limited to agar, agarose, dextran, starch, cellulose, pullulan, etc, and stabilized variants of these.

The formats for solid support matrices can be of any suitable well-known kind. Such solid support matrix for coupling the Ig binding protein of the invention might comprise for example, one of the following: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads. Suitable particle sizes may be in the diameter range of 5-500 μm, such as 10-100 μm, e.g. 20-80 μm. Matrices in particle form can be used as a packed bed or in a suspended form including expanded beds.

In an alternative embodiment, the solid support matrix is a membrane, for example a hydrogel membrane. In some embodiments, the affinity purification involves a membrane as matrix to which the alkaline stable Ig binding protein of the first aspect is covalently bound. The solid support can also be in the form of a membrane in a cartridge.

In some embodiments, the affinity purification involves a chromatography column containing a solid support matrix to which the alkaline stable Ig binding protein of the first aspect is covalently bound.

The alkaline stable Ig binding protein of the invention may be attached to a suitable solid support matrix via conventional coupling techniques utilising, e.g. amino-, sulfhydroxy-, and/or carboxy-groups present in the Ig binding protein of the invention. The coupling may be carried out via a nitrogen, oxygen, or sulphur atom of the Ig binding protein. Preferably, amino acids comprised in an N- or C-terminal peptide linker comprise said nitrogen, oxygen, or sulphur atom.

The Ig binding proteins may be coupled to the support matrix directly or indirectly via a spacer element to provide an appropriate distance between the matrix surface and the Ig binding protein of the invention which improves the availability of the Ig binding protein and facilitates the chemical coupling of the Ig binding protein of the invention to the support.

Methods for immobilization of protein ligands to solid supports are well-known in this field and easily performed by the skilled person in this field using standard techniques and equipment. Depending on the Ig binding protein and on the specific conditions, the coupling may be a multipoint coupling, for example via several lysines, or a single point coupling, for example via cysteine.

Use of the Alkaline Stable Ig Binding Protein.

In a third aspect the present invention is directed to the use of the alkaline stable Ig binding protein of the first aspect or an affinity matrix of the second aspect for affinity purification of immunoglobulins or variants thereof, i.e. the Ig binding protein of the invention is used for affinity chromatography. In some embodiments, the Ig binding protein of the invention is immobilized onto a solid support as described in the second aspect of the invention.

Method of Affinity Purification of Immunoglobulins.

In a fourth aspect the present invention is directed to a method of affinity purification of immunoglobulins, the method comprising (a) providing a liquid containing an immunoglobulin; (b) providing an affinity separation matrix comprising an immobilized alkaline stable Ig binding protein of the first aspect coupled to said affinity separation matrix; (c) contacting said liquid with said affinity separation matrix, wherein said immunoglobulin binds to said immobilized Ig binding protein; and (d) eluting said immunoglobulin from said matrix, thereby obtaining an eluate containing said immunoglobulin. In some embodiments, the method of affinity purification may further comprising one or more washing steps carried out between steps (c) and (d) under conditions sufficient to remove from the affinity separation matrix some or all molecules that are non-specifically bound thereto. Non-specifically bound means any binding that does not involve an interaction between the at least one binding domain of the presently disclosed subject matter and an Immunoglobulin.

Affinity separation matrixes suitable for the disclosed uses and methods are those matrixes according to the embodiments described above and as known to someone skilled in the art. In some embodiments of the fourth aspect, the elution of the immunoglobulin from the matrix in step (d) is effected through a change in pH and/or a change in salt concentration. Any suitable solution used for elution from Protein A media can be used, for example by a solution with pH 5 or lower, or by a solution with pH 11 or higher.

In some embodiments, a further step (f) for efficient cleaning the affinity matrix is added, preferably by using an alkaline liquid, for example, with pH of 13-14. In certain embodiments, the cleaning liquid comprises 0.1-1.0 M NaOH or KOH, preferably 0.25-0.5 M NaOH or KOH. Due to the high alkaline stability of the Ig binding proteins of the invention, such strong alkaline solution can be used for cleaning purposes.

In some embodiments, the affinity matrix can be re-used at least 10 times, at least 20 times, at least 30 times, at least 40 times, at least 50 times, at least 60 times, at least 70 times, at least 80 times, at least 90 times, or at least 100 times, due to a repetition of steps (a) to (e), optionally (a) to (f) can be repeated at least 10 times, at least 20 times, at least 30 times, at least 40 times, at least 50 times, at least 60 times, at least 70 times, at least 80 times, at least 90 times, or at least 100 times.

In general, suitable conditions for performing the method of affinity purification are well known to someone skilled in the art and in particular to someone skilled in Protein A chromatography.

Nucleic Acid Molecule.

In a fifth aspect, the present invention is directed to a nucleic acid molecule, preferably an isolated nucleic acid molecule, encoding an alkaline stable Ig binding protein of any embodiment disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector. In a sixth aspect, the present invention is directed to an expression system which comprises a nucleic acid or a vector as disclosed above, for example a prokaryotic host cell, for example *E. coli*, or a eukaryotic host, for example yeast *Saccharomyces cerevisiae* or *Pichia pastoris* or mammalian cells such as CHO cells.

Method for the Production of an Alkaline Stable Ig Binding Protein.

In a seventh aspect the present invention is directed to a method for the production of an alkaline stable Ig binding protein of the invention, comprising the step(s): (a) culturing the host cell of the sixth aspect under suitable conditions for the expression of the binding protein in order to obtain said alkaline stable Ig binding protein; and (b) optionally isolating said alkaline stable Ig binding protein. Suitable conditions for culturing a prokaryotic or eukaryotic host are well-known to the person skilled in the art.

Ig binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

One embodiment of the present invention is directed to a method for the preparation of an alkaline-stable Ig binding protein according to the invention as detailed above, said method comprising the following steps: (a) preparing a nucleic acid encoding an Ig binding protein as defined above; (b) introducing said nucleic acid into an expression vector; (c) introducing said expression vector into a host cell; (d) cultivating the host cell; (e) subjecting the host cell to culturing conditions under which an Ig binding protein is expressed, thereby (e) producing an Ig binding protein as described above; optionally (f) isolating the protein produced in step (e); and (g) optionally conjugating the protein to solid matrices as described above.

In a further embodiment of the present invention the production of the alkaline stable Ig binding protein is performed by cell-free in vitro transcription/translation.

EXAMPLES

The following Examples are provided for further illustration of the invention. The invention, however, is not limited thereto, and the following Examples merely show the practicability of the invention on the basis of the above description.

Example 1. Generation of Parental Proteins by Shuffling

Parental proteins (e.g. SEQ ID NOs: 3, 4, 10, 14, 21, 22, 25, 47-50) were initially generated by a shuffling process of naturally occurring Protein A domains and Protein A domain variants (e.g. Z domain or other domains with at least 89.5% identity to any naturally occurring domain, e.g. Z/2 domain). In more detail, the shuffling process as understood herein is an assembly process resulting in artificial amino acid sequences starting from a set of non-identical known amino acid sequences. The shuffling process comprised the following steps: a) providing sequences of five naturally occurring Protein A domains E, B, D, A, and C, and Protein A variant domain Z or Z/2; b) alignment of said sequences; c) statistical fragmentation in silico to identify subsequences that were recombined, and then d) assembly of new, artificial sequences of the various fragments to produce a mosaic product, i.e. a novel amino acid sequence. The fragments generated in step c) were of any length, e.g. if the fragmented parent sequence had a length of n, the fragments was of length 1 to n-1.

The relative positions of the amino acids in the mosaic products were maintained with respect to the starting amino acid sequences. At least 90% of positions Q9, Q10, A12, F13, Y14, L17, P20, L22, Q26, R27, F30, I31, Q32, S33, L34, K35, D36, D37, P38, S39, S41, L45, E47, A48, K50, L51, Q55, A56, P57 are identical between the artificial amino acid sequences of for example IB14, IB25, IB74h1, IB74h2, IB47h3, IB47h4, or/and IB27, and naturally occurring Protein A domains or Protein A domain variants. The overall amino acid sequence of the Ig binding proteins IB14, IB25, IB74h1, IB74h2, IB47h3, IB48h4, and IB27 is artificial in that it is not more than 85% identical to the overall amino acid sequence of any of the naturally occurring Protein A domains or domain Z. After the initial artificial Ig binding proteins was generated, the protein was further modified by site-specific randomization of the amino acid sequence to further modify the binding properties. The further modifications were introduced by site-saturation mutagenesis of individual amino acid residues.

Genes for the Ig binding proteins IB14, IB25, IB47, IB74 or/and IB27 as well as SEQ ID NOs: 5-8 were synthesized and cloned into an E. coli expression vector using standard methods known to a skilled person. DNA sequencing was used to verify the correct sequence of inserted fragments.

To generate multimeric Ig binding proteins, 2, 3, 4, 5, or 6 identical Ig binding domains (for example, of SEQ ID NOs: 14, 20, 30) were genetically fused via amino acid linkers.

For specific membrane attachment and purification, a short peptide linker with C-terminal Cys (ASPAPSAPSAC; SEQ ID NO: 41) and optionally a strep-tag (WSHPQFEK; SEQ ID NO: 46) were added to the C-terminus of the Ig binding proteins (for example, see SEQ ID NOs: 39-40). In other embodiments, for specific membrane attachment and purification, positions 43, 46, or 47 were substituted with a cysteine (see for example, SEQ ID NOs: 53-54).

Example 2. Mutagenesis to Generate Variants

For site-directed mutagenesis, the Q5® site-directed Mutagenesis Kit (NEB; Cat. No. E0554S) was used according to the manufacturer's instructions. PCRs were carried out with oligonucleotides coding for each specific substitution respectively and a plasmid containing SEQ ID NO: 14 as template. Products were ligated and transformed into E. coli XL2-blue cells (Stratagene) via electroporation. Single colonies were isolated and DNA sequencing was used for insert containing clones to verify the correct sequences. Results are shown in FIG. 2. A combination of several point mutations was generated by GeneArt™ Strings™ synthesis (Thermo Fisher Scientific). The Strings DNA fragments corresponded to a purified PCR product and were cloned into a derivate of a pET28a vector. Ligation products were transformed into E. coli XL2-blue cells via electroporation. Single colonies were screened by PCR to identify constructs containing inserts of the right size. DNA sequencing was used to verify the correct sequences. Variants with point mutations are shown for example in SEQ ID NO: 9-13, 15-17, and 21.

Example 3. Expression of Ig Binding Proteins

BL21 (DE3) competent cells were transformed with an expression plasmid encoding Ig binding proteins. Cells were spread onto selective agar plates (Kanamycin) and incubated overnight at 37° C. Precultures were inoculated from single colony in 100 ml 2xYT medium and cultured for 16 hours at 37° C. at 160 rpm in a conventional orbital shaker in baffled 1 L Erlenmeyer flasks supplemented with 150 µg/ml Kanamycin without lactose and antifoam. The $OD_{600}$ readout should be in the range of 6-12. Main culture was inoculated from previous overnight culture with an adjusted start-$OD_{600}$ of 0.5 in 400 ml superrich medium (modified H15 medium 2% Glucose, 5% Yeast extract, 0.89% Glycerol, 0.76% Lactose, 250 mM MOPS, 202 mM TRIS, pH 7.4, Antifoam SE15) in 1 L thick-walled Erlenmeyer flasks that was supplemented with 150 µg/ml Kanamycin. Cultures were transferred to a resonant acoustic mixer (RAMbio) and incubated at 37° C. with 20×g. Aeration was facilitated by Oxy-Pump stoppers. Recombinant protein expression was induced by metabolizing glucose and subsequently allowing lactose to enter the cells. At predefined time points $OD_{600}$ was measured, samples adjusted to $5/OD_{600}$ were withdrawn, pelleted and frozen at -20° C. Cells were grown overnight for approx. 24 hours to reach a final $OD_{600}$ of about 45-60. To collect biomass cells were centrifuged at 16000×g for 10 min at 20° C. Pellets were weighed (wet weight) and pH was measured in the supernatant. Cells were stored at -20° C. before processing.

Example 4: SDS-PAGE Analysis of Expression and Solubility of Ig Binding Proteins Samples taken during fermentation were resuspended in 300 µl extraction buffer (PBS supplemented with 0.2 mg/ml Lysozyme, 0.5× BugBuster, 7.5 mM $MgSO_4$, 40 U Benzonase) and solubilized by agitation in a thermomixer at 700 rpm, rt for 15 min. Soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 2 mM EDTA, pH 8.5). 50 µl were taken both from the soluble and insoluble fraction, and 12 µl 5× sample buffer as well as 5 µl 0.5 M DTT were added. Samples were boiled at 95° C. for 5 min. Finally, 8 µl of those samples were applied to NuPage Novex 4-12% Bis-Tris SDS gels which were run in accordance to the manufacturer's recommendations and stained with Coomassie. High level expression of all Ig binding proteins was found under optimized conditions within the chosen period of time (data not shown). All expressed Ig binding proteins were soluble to more than 95% according to SDS-PAGE.

Example 5: Purification of Ig Binding Proteins

Ig binding proteins were expressed in the soluble fraction of *E. coli* with a C-terminal StrepTagII (WSHPQFEK; SEQ ID NO: 46). The cells were lysed by two freeze/thaw cycles and the purification step was performed with Strep-Tactin®-resin according to the manufacturer's instructions (IBA, Goettingen, Germany). To avoid disulfide formation the buffers were supplemented with 1 mM DTT.

Alternatively, Ig binding proteins were expressed in the soluble fraction of *E. coli* with a C-terminal StrepTagII (SEQ ID NO: 46). The cells were resuspended in cell disruption buffer and lysed by a constant cell disruption system (Unit F8B, Holly Farm Business Park) at 1 kbar for two cycles. Purification step was performed with Strep-Tactin-resin (IBA, Goettingen, Germany) and additional gel filtration (Superdex 75 16/60; GE Healthcare) using an AKTAxpress system (Ge Healthcare) according to the manufacturer's instructions. To avoid disulfide formation buffers for Strep-Tactin-purification were supplemented with 1 mM DTT and citrate-buffer (20 mM Citrat, 150 mM NaCl, pH 6.0) was used as running buffer for gel filtration.

Example 6. The Ig Binding Proteins Bind to IgG with High Affinities (as Determined by ELISA)

The affinities of the Ig binding proteins towards $IgG_1$ or $IgG_2$ or $IgG_4$ were determined using an Enzyme Linked Immunosorbent Assay (ELISA). $IgG_1$ or $IgG_2$ or $IgG_4$ containing antibodies (e.g. Cetuximab for $IgG_1$, Panitumumab for $IgG_2$, or Natalizumab for $IgG_4$) were immobilized on a 96 well Nunc MaxiSorb ELISA plate (2 µg/ml). After incubation for 16 h at 4° C. the wells were washed three times with PBST (PBS+0.1% Tween 20) and the wells were blocked with 3% BSA in PBS (2 h at room temperature). The negative controls were wells blocked only with BSA. After blocking, the wells were washed three times with PBST and incubated for 1 h with the Ig binding protein (in PBST) at room temperature. After incubation the wells were washed three times with PBST and subsequently incubated with Strep-Tactin-HRP (1:10000) (IBA, Goettingen, Germany) for 1 h at room temperature. Afterwards the wells were washed three times with PBST and three times with PBS. The activity of the horseradish peroxidase was visualized by adding TMB-Plus substrate. After 30 min the reaction was stopped by adding 0.2 M $H_2SO_4$ and the absorbance was measured at 450 nm. As determined via ELISA, the $K_D$ for human IgG, is 4.9 nM for SEQ ID NO: 14; 3.4 nM for domain Z; 3.1 nM for domain B; and 2.8 nM for domain C.

Example 7. The Ig Binding Proteins Bind to IgG with High Affinities (as Determined with Surface Plasmon Resonance Experiments)

A CM5 sensor chip (GE Healthcare) was equilibrated with SPR running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization removes non-covalently bound Ig binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (µl/min). After each run, the chip surface was regenerated with regeneration buffer and equilibrated with running buffer. The control samples were applied to the matrix. Regeneration and re-equilibration were performed as previously mentioned. Binding studies were carried out by the use of the Biacore® 3000 (GE Healthcare) at 25° C.; data evaluation was operated via the BIAevaluation 3.0 software, provided by the manufacturer, by the use of the Langmuir 1:1 model (RI=0). Evaluated dissociation constants ($K_D$) were standardized against off-target and $K_D$ values of different artificial alkaline stable Ig binding proteins for human $IgG_1$-Fc, Cetuximab ($IgG_1$), Natalizumab ($IgG_4$), or Panitumomab ($IgG_2$) are shown in Table 2.

TABLE 2

$K_D$ values of Ig binding proteins for Ig

| SEQ ID NO: | Ig binding protein | IgG1 (nM) | IgG4 (nM) | IgG2 (nM) |
| --- | --- | --- | --- | --- |
| 20 | cs14 | 2.9 | 2.51 | 7.42 |
| 30 | cs27 | 3.64 | 2.54 | 21.6 |
| 26 | cs25 | 4.24 | 3.27 | 11.6 |
| 45 | cs47h4 | 4.1 | 3.11 | 25.2 |
| 44 | cs47h3 | 4.78 | 4.05 | 20.3 |
| 43 | cs74h2 | 3.48 | 2.72 | 17.2 |
| 42 | cs74h1 | 1.64 | 1.2 | 12.8 |

Example 8. Alkaline Stability of Ig Binding Proteins Coupled to an Epoxy-Activated Matrix Purified Ig binding proteins were coupled to epoxy-activated matrix (Sepharose 6B, GE; Cat. No. 17-0480-01) according to the manufacturer's instructions (coupling conditions: pH 9.0 overnight, blocking for 5 h with ethanolamine). Cetuximab was used as IgG sample (5 mg; 1 mg/ml matrix). Cetuximab was applied in saturated amounts to the matrix comprising immobilized Ig binding protein. The matrix was washed with 100 mM glycine buffer, pH 2.5 to elute cetuximab that was bound to the immobilized IgG-binding protein. The concentration of the eluted IgG was measured by BLI (quantification with Protein A Octet-sensors and Cetuximab as standard) in order to determine the binding activity of the Ig binding proteins. Columns were incubated with 0.5 M NaOH for 6 h at room temperature (22° C.+/−3° C.). The Ig binding activity of the immobilized proteins was analyzed before and after incubation with 0.5 M NaOH for 6 h. The Ig binding activity of immobilized proteins before NaOH treatment was defined as 100%.

FIG. 2 shows the analysis of the alkaline stability of point mutation variants of IB14 (SEQ ID NO: 14). The remaining activity (in %) of Ig binding after six hours of continuous 0.5 M NaOH treatment of point mutations in positions 1, 11, 35, and 42 of IB14 is compared to parental IB14. Substitutions P1I, S11E, S11I, S11A, K35I, K35R, or K42L improve the Ig binding activity by at least about 25%.

FIG. 3 shows that the activity of for example variant proteins with combinations of 3, 4, or 5 substitutions in positions 1, 11, 28, 35, and/or 42 was higher compared to the activity of the parental protein IB14 (SEQ ID NO: 14). Ig binding protein cs14-1 (SEQ ID NO: 18) showed about at least 50%, cs14-2 (SEQ ID NO: 19) showed about at least 70%, cs14-3 (SEQ ID NO: 20) showed about at least 80% higher Ig binding activity compared to the IB14 after incubation for 6 h at 0.5 M NaOH.

FIG. 4 shows that the activity of variant Ig binding proteins with combinations of 3, 4, or 5 substitutions in positions 1, 11, 35, and/or 42 was higher compared to the activity of the parental protein IB27. cs27-1 (SEQ ID NO: 29) showed about at least 30% and cs27-2 (SEQ ID NO: 30) showed about at least 40% higher Ig binding activity compared to the parental protein after incubation for 6 h at 0.5 M NaOH.

FIG. 5 shows that the activity of variant Ig binding proteins with combinations of 1I, 11A, 35R, and 42L was higher compared to the activity of the parental protein, here shown as IB14 (other parental proteins are comparable to 1IB14; data not shown). Ig binding proteins cs74h1 (SEQ ID NO: 42), cs74h2 (SEQ ID NO: 43), cs47h3 (SEQ ID NO: 44), cs47h4 (SEQ ID NO: 45), and cs25 (SEQ ID NO: 26) showed significantly higher Ig binding activity compared to IB14 after incubation for 6 h at 0.5 M NaOH.

The invention claimed is:

1. An Immunoglobulin (Ig) binding protein comprising one or more Ig binding domains, wherein at least one Ig binding domain comprises SEQ ID NO: 1 or SEQ ID NO: 2 having 3 or 4 substitutions, wherein the 3 or 4 substitutions are selected from the group consisting of an amino acid substitution to Isoleucine at position 1, an amino acid substitution to Alanine, Glutamic Acid, or Isoleucine at position 11, an amino acid substitution to Arginine or Isoleucine at position 35, and an amino acid substitution to Leucine at position 42, and optionally wherein said at least one Ig binding domain further comprises 1 or 2 additional amino acid sequence modifications, wherein each individual amino acid sequence modification is selected from the group consisting of a single amino acid substitution, a single amino acid deletion, and a single amino acid insertion.

2. The Ig binding protein of claim 1, wherein said at least one Ig binding domain comprises an amino acid sequence selected from the group consisting of SEQ ID NO: 3, 4, 10, 14, 21, 25, 47, 48, 49, and 50 having 3 or 4 amino acid substitutions, wherein the 3 or 4 amino acid substitutions are selected from the group consisting of an amino acid substitution of Alanine or Praoline to Isoleucine at position 1, an amino acid substitution of Serine to Alanine, Glutamic Acid, or Isoleucine at position 11, an amino acid substitution of Lysine at position 35 to Arginine or Isoleucine, and an amino acid substitution of Lysine to Leucine at position 42.

3. The Ig binding protein of claim 1, wherein said at least one Ig binding domain comprises an amino acid sequence of any one of SEQ ID NOs: 5-8 with 3 or 4 amino acid substitutions, wherein the 3 or 4 amino acid substitutions are selected from the group consisting of an amino acid substitution to Isoleucine at position 1, an amino acid substitution to Alanine, Glutamic Acid, or Isoleucine at position 11, an amino acid substitution at position 35 to Arginine or Isoleucine, and an amino acid substitution to Leucine at position 42.

4. The Ig binding protein of claim 1, wherein the 3 or 4 substitutions and the optional 1 or 2 additional amino acid modifications are selected from the group consisting of 1I/11A/35R; 1I/11E/35R; 1I/11I/35R; 1I/11A/42L; 1I/11E/42L; 1I/11I/42L; 1I/11A/35I; 1I/11E/35I; 1/11I/35I; 1I/35R/42L; 1I/35I/42L; 11I/35R/42L; 11I/35I/42L; 11I/35R/42L; 11A/35I/42L; 11E/35R/42L; 11E/35I/42L; 1I/11A/35R/42L; 1I/11E/35R/42L; 1I/11I/35R/42L; 1I/11A/35I/42L; 1I/11E/35I/42L; 1I/11I/35I/42L; 1I/11A/28N/35R/42L; 1I/11E/28N/35R/42L; 1I/11I/28N/35R/42L; 1I/11A/28N/35I/42L; 1I/11I/28N/351/42L; and 1I/11E/28N/35I/42L.

5. The Ig binding protein of claim 4, wherein the 3 or 4 of the amino acid positions are selected from the group consisting of 1I, 11A, 35R, and 42L.

6. The Ig binding protein of claim 1, wherein said at least one Ig binding domain further comprises 1 or 2 additional amino acid sequence modifications, wherein each individual amino acid sequence modification is selected from the group consisting of a single amino acid substitution, a single amino acid deletion, and a single amino acid insertion.

7. The Ig binding protein of claim 1, wherein said at least one Ig binding domain comprises the amino acid sequence as set forth in SEQ ID NO: 20, or a sequence at least 96% identical thereto.

8. The Ig binding protein of claim 1, wherein said at least one Ig binding domain comprises the amino acid sequence as set forth in SEQ ID NO: 30, or a sequence at least 94% identical thereto.

9. The Ig binding protein of claim 1, wherein said at least one Ig binding domain comprises the amino acid sequence as set forth in SEQ ID NO: 26, or a sequence at least 98% identical thereto.

10. The Ig binding protein of claim 1, wherein said at least one Ig binding domain comprises the amino acid sequence as set forth in SEQ ID NO: 44, or a sequence at least 98% identical thereto.

11. The Ig binding protein of claim 1, wherein said at least one Ig binding domain comprises the amino acid sequence as set forth in SEQ ID NO: 43, or a sequence at least 98% identical thereto.

12. The Ig binding protein of claim 1, wherein the protein comprises 2, 3, 4, 5, 6, 7, or 8 Ig binding domains linked to each other.

13. The Ig binding protein of claim 1, wherein the protein is conjugated to a solid support.

14. The Ig binding protein of claim 13, wherein said Ig binding protein further comprises an attachment site for site-specific covalent coupling of said Ig binding protein to a solid support.

15. The Ig binding protein of claim 1, wherein said Ig binding protein binds to IgG1, IgG2, IgG4, IgM, IgA, Ig fragments comprising the Fc region, fusion proteins comprising an Fc region of an Ig, and conjugates comprising an Fc region of an Ig.

16. An affinity separation matrix comprising the Ig binding protein as defined in claim 1.

17. An Immunoglobulin (Ig) binding protein comprising one or more Ig binding domains, wherein at least one Ig binding domain comprises SEQ ID NO: 2 having 3 or 4 substitutions, wherein the 3 or 4 substitutions are selected from the group consisting of an amino acid substitution to Isoleucine at position 1, an amino acid substitution to Alanine, Glutamic Acid, or Isoleucine at position 11, an amino acid substitution to Arginine or Isoleucine at position 35, and an amino acid substitution to Leucine at position 42.

18. An Ig binding protein comprising one or more Ig binding domains, wherein at least one Ig binding domain comprises an amino acid sequence of SEQ ID NO: 52, wherein the amino acid at position 5 is selected from H or F, the amino acid at position 7 is selected from K or E, the amino acid at position 8 is selected from D, A, or E, the amino acid at position 25 is selected from D or E, the amino acid at position 28 is selected from S or N, the amino acid at position 42 is selected from L or K, the amino acid at position 44 is selected from I or V, the amino acid at position 46 is selected from G or A, the amino acid at position 49 is selected from K or Q, the amino acid at position 54 is selected from A or S, and the amino acid at position 58 is selected from P or K.

19. The Ig binding protein of claim 18, wherein said at least one Ig binding domain comprises an amino acid sequence selected from the group consisting of SEQ ID NOs: 20, 26, 30, and 42-45 or an amino acid sequence at least 89.5% identical thereto.

20. A method of affinity purification of immunoglobulins, the method comprising:
(a) providing a liquid containing immunoglobulins;
(b) providing an affinity separation matrix comprising at least one Ig binding protein of claim 1 coupled to said affinity separation matrix;
(c) contacting said liquid and said affinity separation matrix, wherein said immunoglobulin binds to said Ig binding protein; and
(d) eluting said immunoglobulin from said matrix, thereby obtaining an eluate containing said immunoglobulin.

21. The method of claim 20, further comprising washing the affinity matrix between steps (c) and (d) under conditions sufficient to remove from the affinity separation matrix some or all molecules that are non-specifically bound thereto.

* * * * *